(12) United States Patent
Robb et al.

(10) Patent No.: US 11,834,442 B2
(45) Date of Patent: Dec. 5, 2023

(54) MECHANICAL REGULATION OF PHOTOSWITCHING

(71) Applicant: California Institute of Technology, Pasadena, CA (US)

(72) Inventors: Maxwell J. Robb, Altadena, CA (US); Xiaoran Hu, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 285 days.

(21) Appl. No.: 17/019,107

(22) Filed: Sep. 11, 2020

(65) Prior Publication Data

US 2021/0070741 A1 Mar. 11, 2021

Related U.S. Application Data

(60) Provisional application No. 62/898,745, filed on Sep. 11, 2019.

(51) Int. Cl.
*C07D 409/14* (2006.01)
*G01L 1/24* (2006.01)

(52) U.S. Cl.
CPC .............. *C07D 409/14* (2013.01); *G01L 1/24* (2013.01)

(58) Field of Classification Search
None
See application file for complete search history.

(56) References Cited

PUBLICATIONS

Asadirad, Amir Mahmoud, et al. "Controlling a polymer adhesive using light and a molecular switch." Journal of the American Chemical Society 136.8 (2014): 3024-3027. (Year: 2014).*

Erno, Zach, et al. "Using light and a molecular switch to 'lock' and 'unlock' the Diels-Alder reaction." Organic & Biomolecular Chemistry 10.14 (2012): 2787-2792. (Year: 2012).*

Kida, Jumpei, et al. "The photoregulation of a mechanochemical polymer scission." Nature Communications 9.1 (2018): 3504. (Year: 2018).*

Hu, Xiaoran, et al. "Mechanochemical regulation of a photochemical reaction." Journal of the American Chemical Society 140.43 (2018): 14073-14077. (Year: 2018).*

Berkowski et al., "Ultrasound-Induced Site-Specific Cleavage of Azo-Functionalized Poly(ethylene glycol)", Macromolecules, Sep. 27, 2005, vol. 38, No. 22, pp. 8975-8978, https://doi.org/10.1021/ma051394n.

Beyer, "The mechanical strength of a covalent bond calculated by density functional theory", Journal of Chemical Physics, 2002, vol. 112, pp. 7307-7312, https://doi.org/10.1063/1.481330.

Beyer et al., "Mechanochemistry: The Mechanical Activation of Covalent Bonds", Chem. Rev., Jul. 19, 2005, vol. 105, No. 8, pp. 2921-2948, https://doi.org/10.1021/cr030697h.

Caruso et al., "Mechanically-Induced Chemical Changes in Polymeric Materials", Chem. Rev., Oct. 14, 2009, vol. 109, No. 11, pp. 5755-5798, https://doi.org/10.1021/cr9001353.

(Continued)

*Primary Examiner* — Robert S Loewe

(57) ABSTRACT

A mechanochemically-gated photoswitching molecular system is described, along with the methods for the synthesis and use thereof. This molecular system comprises a thermally stable diarylethene-dienophile Diels-Alder adduct mechanophore embedded into a polymer chain or network, wherein the mechanophore undergoes the retro [4+2] cycloaddition reaction under mechanical force to reveal a diarylethene photoswitch.

29 Claims, 15 Drawing Sheets

(56) References Cited

PUBLICATIONS

Chen et al., "Mechanically induced chemiluminescene from polymers incorporating a 1,2 dioxetane unit in the main chain", Nature Chemistry, 2012, vol. 4, pp. 559-562, published online Jun. 3, 2012, DOI:10.1038/NCHEM.1358.

Chen et al., "Mechanochemical unzipping of insulating polyladderene to semiconducting polyacetylene", Science, Aug. 4, 2017, vol. 357, Issue 6350, pp. 475-479, DOI: 10.1126/science.aan2797.

Davis et al., "Force-induced activation of covalent bonds in mechanoresponsive polymeric materials", Nature, May 7, 2009, vol. 459, Issue 7243, pp. 68-72, doi: 10.1038/nature07970.

Diesendruck et al., "Proton-Coupled Mechanochemical Transduction: A Mechanogenerated Acid", Journal of the American Chemical Society, Jul. 9, 2012, vol. 134, No. 30, pp. 12446-12449, https://doi.org/10.1021/ja305645x.

Duan et al., "An Investigation of the Selective Chain Scission at Centered Diels-Alder Mechanophore under Ultrasonication", Macromolecules Feb. 9, 2017, vol. 50, No. 4, pp. 1353-1361, https://doi.org/10.1021/acs.macromol.6b0237.

Gossweiler et al., "Mechanochemical Activation of Covalent Bonds in Polymers with Full and Repeatable Macroscopic Shape Recovery", ACS Macro Letters, 2014, vol. 3, pp. 216-219, dx.doi.org/10.1021/mz500031q.

Gostl et al., "Controlling covalent connection and disconnection with light", Angew. Chem. International Edition, Aug. 11, 2014, vol. 53, Issue 33, pp. 8784-8787, https://doi.org/10.1002/anie.201310626.

Heo et al., "Self-Healing Polyurethanes with Shape Recovery", Advanced Function Materials, May 30, 2014, vol. 24, Issue 33, pp. 5261-5268, https://doi.org/10.1002/adfm.201400299.

Hickenboth et al., "Biasing reaction pathways with mechanical force", Nature, Mar. 22, 2007, vol. 446, Issue 7134, pp. 423-427, doi: 10.1038/nature05681.

Imato et al., "Mechanophores with a Reversible Radical System and Freezing-Induced Mechanochemistry in Polymer Solutions and Gels", Angew Chem Int Ed Engl., May 18, 2015; vol. 54, Issue 21, pp. 6168-6172, published online Mar. 30, 2015, doi: 10.1002/anie.201412413.

Irie et al., "Blocked photochromism of diarylethenes", Journal of the American Chemical Society, Oct. 1, 1992, vol. 114, No. 22, pp. 8715-8716, https://doi.org/10.1021/ja00048a063.

Irie et al., "Photochromism of Diarylethene Molecules and Crystals: Memories, Switches, and Actuators", Chemical Reviews, Dec. 16, 2014, vol. 114, No. 24, pp. 12174-12277, https://doi.org/10.1021/cr500249p (Presented in Two Parts).

Kawai et al., "Photochemical pKa-Modulation and Gated Photochromic Properties of a Novel Diarylethene Switch", European Journal of Organic Chemistry, Sep. 1999, vol. 999, Issue 9, pp. 2359-2366, published online Aug. 12, 1999, https://doi.org/10.1002/(SICI)1099-0690(199909)1999:9<2359::AID-EJOC2359>3.0.CO;2-%23.

Kida et al., "The photoregulation of a mechanochemical polymer scission", Nature Communications, 2018, vol. 9, No. 3504, 6 pgs., DOI: 10.1038/s41467-018-05996-7.

Kobatake et al., "Acid-induced photochromic system switching of diarylethene derivatives between P- and T-types", Chemical Communications, Feb. 2007, pp. 1698-1700, DOI: 10.1039/b700177k.

Konda et al., "Molecular Catch Bonds and the Anti-Hammond Effect in Polymer Mechanochemistry", Journal of the American Chemical Society, Aug. 2, 2013, vol. 135, No. 34, pp. 12722-12729, https://doi.org/10.1021/ja4051108.

Kryger et al., "Structure—Mechanochemical Activity Relationships for Cyclobutane Mechanophores", Journal of the American Chemical Society, Oct. 27, 2011, vol. 133, No. 46, pp. 18992-18998, https://doi.org/10.1021/ja2086728.

Kuhni et al., "Gated Photochromism of 1,2-Diarylethenes", Organic Letters, Apr. 21, 2007, vol. 9, No. 10, pp. 1915-1918, https://doi.org/10.1021/ol070339r.

Larsen et al., ""Flex-activated" mechanophores: using polymer mechanochemistry to direct bond bending activation", Journal of the American Chemical Society, 3 Jun. 5, 2013, vol. 135, No. 22, pp. 8189-8192, published online May 23, 2013, doi: 10.1021/ja403757p.

Lemieux et al., "Reactivity-Gated Photochromism of 1,2-Dithienylethenes for Potential Use in Dosimetry Applications", Organic Letters, Jun. 14, 2005, vol. 7, No. 14, pp. 2969-2972, https://doi.org/10.1021/ol050971p.

Lemieux et al., "Selective and Sequential Photorelease Using Molecular Switches", Angew. Chem. International Edition, Oct. 17, 2006, vol. 45, Issue 41, pp. 6820-6824, https://doi.org/10.1002/anie.200601584.

Li et al., "Mechanophore Activation at Heterointerfaces", Journal of the American Chemical Society, Oct. 31, 2014, vol. 136, No. 45, pp. 15925-15928, https://doi.org/10.1021/ja509949d.

Li et al., "Polymer Mechanochemistry: From Destructive to Productive", Acc. Chem. Res. Jul. 15, 2015, vol. 48, No. 8, pp. 2181-2190, https://doi.org/10.1021/acs.accounts.5b00184.

Ohsumi et al., "Chemical control of the photochromic reactivity of diarylethene derivatives", Chemical Communications, Jul. 9, 2005, pp. 3921-3923, DOI: 10.1039/n506801k.

Peterson et al., "3D-Printed Mechanochromic Materials", ACS Applied Materials and Interfaces, Dec. 5, 2014, vol. 7, pp. 577-583, dx.doi.org/10.1021/am506745m.

Ramirez et al., "Mechanochemical strengthening of a synthetic polymer in response to typically destructive shear forces", Nature Chemistry, 2013, vol. 5, pp. 757-761, published online Aug. 4, 2013. DOI: 10.1038/NCHEM.1720.

Robb et al., "A Retro-Staudinger Cycloaddition: Mechanochemical Cycloelimination of a β-Lactam Mechanophore", Journal of the American Chemical Society, Sep. 2, 2015, vol. 137, Issue 34, pp. 10946-10949, doi: 10.1021/jacs.5b07345.

Robb et al., "Regioisomer-Specific Mechanochromism of Naphthopyran in Polymeric Materials", Journal of the American Chemical Society, Sep. 12, 2016, vol. 138, No. 38, pp. 12328-12331, https://doi.org/10.1021/jacs.6b07610.

Stevenson et al., "Controlling Reactivity by Geometry in Retro-Diels-Alder Reactions under Tension", Journal of the American Chemical Society, Oct. 31, 2017, vol. 139, No. 46, pp. 16768-16771, https://doi.org/10.1021/jacs.7b08895.

Sung et al., "Interfacial Mechanophore Activation Using Laser-Induced Stress Waves", Journal of the American Chemical Society, Mar. 29, 2018, vol. 140, No. 15, pp. 5000-5003, https://doi.org/10.1021/jacs.8b01427.

Wang et al., "Mechanical gating of a mechanochemical reaction cascade", Nature Communications, Nov. 16, 2016, vol. 7, 13433, 8 pgs., DOI: 10.1038/ncomms13433.

Wang et al., "Mechanochemical Strengthening of a Multi-mechanophore Benzocyclobutene Polymer", ACS Macro Lett., Jul. 20, 2015, vol. 4, No. 8, pp. 834-837, https://doi.org/10.1021/acsmacrolett.5b00440.

Wang et al., "Single-Molecule Observation of a Mechanically Activated Cis-to-Trans Cyclopropane Isomerization", Journal of the American Chemical Society, Aug. 8, 2016, vol. 138, No. 33, pp. 10410-10412, https://doi.org/10.1021/jacs.6b0645.

Wollenhaupt et al., "Should the Woodward-Hoffmann Rules be Applied to Mechanochemical Reactions?", ChemPhysChem, May 27, 2015, vol. 16, Issue 8, pp. 1593-1597, https://doi.org/10.1002/cphc.201500362.

Yokoyama et al., "Photochromism of a protonated 5-dimethylaminoindolylfulgide: a model of a non-destructive read-out for a photon mode optical memory", Journal of Chemical Society Chemical Communications, 1991, pp. 1722-1724, https://doi.org/10.1039/C39910001722.

Zhang et al., "Mechanical Susceptibility of a Rotaxane", Journal of the American Chemical Society, Sep. 6, 2019, vol. 141, No. 40, pp. 15879-15883, https://doi.org/10.1021/jacs.9b06960.

Zhang et al., "Mechanochromism and Mechanical-Force-Triggered Cross-Linking from a Single Reactive Moiety Incorporated into Polymer Chains", Angew. Chem. International Edition, Jan. 25, 2016, vol. 55, Issue 9, pp. 3040-3044, https://doi.org/10.1002/anie.201510171.

(56) References Cited

PUBLICATIONS

Akbulatov et al., "Critical review of experimental polymer mechanochemistry and its interpretational frameworks", ChemPhysChen, 2017, vol. 18, pp. 1422-1450.

Alouane et al., "Self-Immolative Spacers: Kinetic Aspects, Structure-Property Relationships, and Applications", Angewandte Chemie International Edition, vol. 54, Issue 26, Jun. 22, 2015, first published Jun. 5, 2015, pp. 7492-7509, https://doi.org/10.1002/anie.201500088.

Binder et al., "A Mechanochemically Triggered "Click" Catalyst", Angewandte Chemie International Edition, vol. 54, Issue 47, Nov. 16, 2015, published online Sep. 30, 2015, pp. 13918-13922, https://doi.org/10.1002/anie.201505678.

Boutelle et al., "Substituent Effects on the Reversibility of Furan-Maleimide Cycloadditions", The Journal of Organic Chemistry, vol. 76, No. 19, Aug. 2011, pp. 7994-8002, DOI: 10.1021/jo201606z.

Cohen et al., "Excited State Proton-Transfer Reactions of Coumarin 4 in Protic Solvents", The Journal of Physical Chemistry A, vol. 105, No. 30, Jul. 7, 2001, pp. 7157-7164, https://doi.org/10.1021/jp010576q.

Deng et al., "A Novel Way to Synthesize Star Polymers in One Pot by ATRP of N-[2-(2-Bromoisobutyryloxy)ethyl]maleimide and Styrene", Macromolecules, vol. 37, No. 1, pp. 18-26, 2004, first published Dec. 13, 2003, https://doi.org/10.1021/ma034542n.

Di Giannantonio et al., "Triggered Metal Ion Release and Oxidation: Ferrocene as a Mechanophore in Polymers", Angewandte Chemie International Edition English, Aug. 27, 2018, vol. 57, No. 35, pp. 11445-11450, published online Jul. 26, 2018, doi: 10.1002/anie.201803524.

Diesendruck et al., "Mechanically triggered heterolytic unzipping of a low-ceiling-temperature polymer", Nature Chemistry, Jul. 2014, vol. 6, pp. 623-628, published online Apr. 28, 2014, DOI: https://doi.org/10.1038/nchem.1938.

Esser-Kahn et al., "Triggered Release from Polymer Capsules", Macromolecules, Jul. 6, 2011, vol. 44, pp. 5539-5553, dx.doi.org/10.1021/ma201014n.

Fan et al., "Thermo-responsive self-immolative nanoassemblies: direct and indirect triggering", Chemical Communications, Oct. 6, 2017, vol. 53, No. 89, 43 pages, 12068-12071, DOI:10.1039/C7CC06410A.

Foster et al., "Irreversibleendo-SelectiveDiels-AlderReactionsof SubstitutedAlkoxyfurans:AGeneralSynthesisofendo-Cantharimides", Chemistry, a European Journal, 2015, vol. 21, pp. 6107-6114, DOI: 10.1002/chem.201406286.

Gostl et al., "π-extended anthracenes as sensitive probes for mechanical stress", Chemical Science, 2016, vol. 7, pp. 370-375, first published Oct. 7, 2015, DOI: 10.1039/c5sc03297k.

Grady et al., "Shockwave Loading of Mechanochemically Active Polymer Coatings", ACS Applied Materials & Interfaces, vol. 6, No. 8, Mar. 26, 2014, pp. 5350-5355, https://doi.org/10.1021/am406028q.

Groote et al., "Mechanocatalysis: forcing latent catalysts into action", Polymer Chemistry, 2013, vol. 4, pp. 4846-4859, doi: 10.1039/C3PY00071K.

Hay et al., "Substituent effects on the kinetics of reductively-initiated fragmentation of nitrobenzyl carbamates designed as triggers for bioreductive prodrugs", Journal of the Chemical Society Perkin Transactions, Jan. 1999, vol. 119, No. 19, pp. 2759-2770, DOI: 10.1039/a904067f.

Hu et al., "Mechanically Triggered Release of Functionally Diverse Molecular Payloads from Masked 2-Furylcarbinol Derivatives", ACS Central Science, Jul. 14, 2021, vol. 7, pp. 1216-1224, doi: 10.1021/acscentsci.1c00460.

Hu et al., "Mechanically Triggered Small Molecule Release from a Masked Furfuryl Carbonate", Journal of the American Chemical Society, vol. 141, No. 38, Sep. 25, 2019, published online Sep. 16, 2019, pp. 15018-15023, doi: 10.1021/jacs.9b08663.

Huo et al., "Mechanochemical bond scission for the activation of drugs", Nature Chemistry, Feb. 2021, vol. 13, pp. 131-139, first published Jan. 29, 2021, https://doi.org/10.1038/s41557-020-00624-8.

Jayathilaka et al., "Force-mediated molecule release from double network hydrogels", Chemical Communications, Sep. 4, 2021, vol. 57, No. 68, pp. 8484-8487, published online Aug. 5, 2021, doi: 10.1039/d1cc02726c.

Kean et al., "A coumarin dimer probe of mechanochemical scission efficiency in the sonochemical activation of chain-centered mechanophore polymers", Chemical Communications, Apr. 29, 2015, vol. 51, Issue 44, pp. 9157-9160, DOI https://doi.org/10.1039/C5CC01836F.

Kim et al., "High-intensity focused ultrasound-induced mechanochemical transduction in synthetic elastomers", PNAS, May 21, 2019, vol. 116, No. 21, pp. 10214-10222, published online May 10, 2019, doi: 10.1073/pnas.1901047116.

Klein et al., "Validation of the CoGEF Method as a Predictive Tool for Polymer Mechanochemistry", Journal of the American Chemical Society, vol. 142, No. 38, Sep. 23, 2020, published online Sep. 9, 2020, pp. 16364-16381, doi: 10.1021/jacs.0c06868.

Larsen et al., "Successive mechanochemical activation and small molecule release in an elastomeric material", Journal of the American Chemical Society, vol. 136, No. 4, Jan. 29, 2014, published online Jan. 16, 2014, pp. 1276-1279, doi: 10.1021/ja411891x.

Lee et al., "Controlled Drug Delivery from Polymers by Mechanical Signals", Advanced Materials, vol. 13, Issue 11, Jun. 2001, first published May 31, 2011, pp. 837-839, https://doi.org/10.1002/1521-4095(200106)13:11<837::AID-ADMA837>3.0.CO;2-D.

Lin et al., "A Latent Mechanoacid for Time-Stamped Mechanochromism and Chemical Signaling in Polymeric Materials", Journal of the American Chemical Society, vol. 142, No. 1, Jan. 8, 2020, published online Dec. 25, 2019, pp. 99-103, doi: 10.1021/jacs.9b12861.

May et al., "Is Molecular Weight or Degree of Polymerization a Better Descriptor of Ultrasound-Induced Mechanochemical Transduction?", ACS Macro Lett. 2016, vol. 5, pp. 177-180, DOI: 10.1021/acsmacrolett.5b00855.

Mcfadden et al., "Force-Dependent Multicolor Mechanochromism from a Single Mechanophore", Journal of the American Chemical Society, vol. 141, No. 29, Jul. 24, 2019, published online Jul. 15, 2019, pp. 11388-11392, doi: 10.1021/jacs.9b05280.

Mosey et al., "Versatile approach to α-alkoxy carbamate synthesis and stimulus-responsive alcohol release", Organic & Molecular Chemistry, Aug. 2012, vol. 10, No. 39, pp. 7980-7985 DOI: 10.1039/c2ob26571k.

Nguyen et al., "Surface-Dependent Kinetics of Cu(0)-Wire-Catalyzed Single-Electron Transfer Living Radical Polymerization of Methyl Acrylate in DMSO at 25° C.", Macromolecules, vol. 42, No. 7, Mar. 17, 2009, pp. 2379-2386, https://doi.org/10.1021/ma8028562.

Nichol et al., "Multi-stimuli responsive trigger for temporally controlled depolymerization of self-immolative polymers", Organic Chemistry, vol. 10, No. 36, Aug. 12, 2019, pp. 4914-4919, https://doi.org/10.1039/C9PY00301K.

Patrick et al., "Polymers with autonomous life-cycle control", Nature, vol. 540, Dec. 15, 2016, pp. 363-370, doi: 10.1038/nature21002.

Peterson et al., "1,2-oxazine linker as a thermal trigger for self-immolative polymers", Polymer, Nov. 5, 2014, vol. 55, Issue 23, pp. 5980-5985, https://doi.org/10.1016/j.polymer.2014.09.048.

Peterson et al., "Kinetic Analysis of Mechanochemical Chain Scission of Linear Poly(phthalaldehyde)", Macromolecular Rapid Communications, vol. 35, Issue 18, Sep. 2014, first published Aug. 11, 2014, pp. 1611-1614, https://doi.org/10.1002/marc.201400271.

Piermattei et al., "Activating catalysts with mechanical force", Nature Chemistry, May 2009, vol. 1, Issue 2, pp. 133-137, published online Apr. 6, 2009, doi: 10.1038/nchem.167.

Ronn et al., "An Expedient Route to 3-Methoxy-2-furaldehyde", Synlett, vol. 1, 2012, Advanced online publication Sep. 12, 2011, pp. 134-136, DOI: 10.1055/s-0031-1290103.

(56) References Cited

PUBLICATIONS

Roth et al., "Dendritic, Oligomeric, and Polymeric Self-Immolative Molecular Amplification", Chemical Reviews, vol. 116, No. 3, Feb. 10, 2016, published online Sep. 10, 2015, pp. 1309-1352, doi: 10.1021/acs.chemrev.5b00372.

Schmid et al., "A self-immolative spacer that enables tunable controlled release of phenols under neutral conditions", The Journal of Organic Chemistry, vol. 77, No. 9, Apr. 2012, pp. 4363-4374, DOI: 10.1021/jo300400q.

Sha et al., "Quantitative and Mechanistic Mechanochemistry in Ferrocene Dissociation", ACS Macro Letters, Oct. 16, 2018, vol. 7, No. 10. pp. 1174-1179, published online Sep. 14, 2018, doi: 10.1021/acsmacrolett.8b00625.

Shi et al., "Mechanochemical activation of disulfide-based multifunctional polymers for theranostic drug release", Chemical Science, vol. 12, 2020, pp. 1668-1674, DOI: 10.1039/d0sc06054b.

Shi et al., "The Mechanochemical Release of Naphthalimide Fluorophores from β-Carbonate and β-Carbamate Disulfide-Centered Polymers", CCS Chemistry, Nov. 2021, vol. 3, Issue 11, pp. 2333-2344, first published Aug. 13, 2021, https://doi.org/10.31635/ccschem.021.202101147.

Shi et al., "Toward Drug Release Using Polymer Mechanochemical Disulfide Scission", The Journal of the American Chemical Society, Aug. 17, 2020, vol. 142, No. 34, p. 14725-14732, DOI: 10.1021/jacs.0c07077.

Sulkanen et al., "Spatially Selective and Density-Controlled Activation of Interfacial Mechanophores", Journal of the American Chemical Society, Mar. 6, 2019, vol. 141, No. 9, pp. 4080-4085, published online Feb. 26, 2019. doi: 10.1021/jacs.8b10257.

Swager, "Sensor Technologies Empowered by Materials and Molecular Innovations", Agnewandte Chemie International Edition, vol. 57, Issue 16, Apr. 9, 2018, first published Feb. 22, 2018, pp. 4248-4257, https://doi.org/10.1002/anie.201711611.

Toohey et al., "Self-healing materials with microvascular networks", Nature Materials, Aug. 2007, vol. 6, published online Jun. 10, 2007, doi:10.1038/nmat1934.

Wang et al., "A Novel Mechanochromic and Photochromic Polymer Film: When Rhodamine Joins Polyurethane", Advanced Materials, vol. 27, Issue 41, Nov. 4, 2015, first published Sep. 24, 2015, pp. 6469-6474, first published Sep. 24, 2015, https://doi.org/10.1002/adma.201503424.

Warford et al., "From Slow to Fast—the User Controls the Rate of the Release of Molecules From Masked Forms Using a Photoswitch and Different Types of Light", Chemical Communications, Mar. 2015, vol. 51, No. 32, pp. 7039-7042.

White et al., "Autonomic healing of polymer composites", Nature, vol. 409, No. 6822, Feb. 15, 2001, pp. 794-797, doi: 10.1038/35057232.

Wu et al., "Molecular stress relief through a force-induced irreversible extension in polymer contour length", Journal of the American Chemical Society, vol. 132, No. 45, Oct. 26, 2010, pp. 15936-15938, https://doi.org/10.1021/ja108429h.

Yang et al., "Benzoladderene Mechanophores: Synthesis, Polymerization, and Mechanochemical Transformation", Journal of the American Chemical Society, vol. 141, No. 16, Apr. 24, 2019, published online Apr. 16, 2019, pp. 6479-6483, doi: 10.1021/jacs.9b01736.

Zanetti et al., "α-Furfuryl Bromide (2-Bromomethylfuran)", Journal of the American Chemical Society, vol. 61, No. 8, Aug. 1, 1939, pp. 2249-2251, https://doi.org/10.1021/ja01877a506.

Zhang et al., "Mechanical Force-Triggered Drug Delivery", Chemical Reviews, Sep. 29, 2016, vol. 116, pp. 12536-12563, doi: 10.1021/acs.chemrev.6b00369.

\* cited by examiner

MECHANICAL REGULATION OF PHOTOSWITCHING

CROSS-REFERENCE TO RELATED APPLICATIONS

The current application claims priority to U.S. Provisional Application No. 62/898,745, filed Sep. 11, 2019, the disclosure of which is incorporated herein by reference in its entirety.

FIELD OF THE INVENTION

The current disclosure is directed to mechanochemically-gated photoswitching molecular systems, and methods for the synthesis and use thereof.

BACKGROUND OF THE INVENTION

Polymer mechanochemistry is an emerging field of research that investigates the use of mechanical force for promoting selective chemical transformations (see, for example, Beyer, M. K. et al., Chem. Rev. 2005, 105, 2921-2948; and Caruso, M. M. et al. Chem. Rev. 2009, 109, 5755-5798, the disclosures of which are incorporated herein by reference). More specifically, this field studies chemical reactions resulting from mechanical stress applied to mechanochemically active molecules (mechanophores), wherein an applied mechanical stress is transduced to a particular covalent bond within a mechanophore via polymer chains attached to such mechanophore (Li, J. et al. Acc. Chem. Res. 2015, 48, 2181-2190, the disclosures of which are incorporated herein by reference). Research has showcased exciting and unique capabilities of polymer mechanochemistry, contributing to new fundamental understanding of molecular reactivity and creating many opportunities for its application. For instance, mechanical force has been shown to bias reaction pathways, facilitating formally symmetry-forbidden pericyclic reactions (see, for example, Hickenboth, C. R. et al. Nature 2007, 446, 423-427; Wang, J. et al. Nat. Chem. 2015, 7, 323-327; and Wollenhaupt, M. et al. ChemPhysChem 2015, 16, 1593-1597, the disclosures of which are incorporated herein by reference). Mechanophores have also been designed to produce color changes (Davis, D. A. et al. Nature 2009, 459, 68-72; Gossweiler, G. R. et al. ACS Macro Lett. 2014, 3, 216-219; Robb, M. J. et al. Am. Chem. Soc. 2016, 138, 12328-12331; Peterson, G. I. et al. ACS Appl. Mater. Interfaces 2015, 7, 577-583; and Imato, K. et al. Angew. Chem. Int. Ed. 2015, 54, 6168-6172, the disclosures of which are incorporated herein by reference) and chemiluminescence (Chen, Y. et al. Nat. Chem. 2012, 4, 559-562, the disclosure of which are incorporated herein by reference) for stress-sensing applications, generate reactive functional groups for self-healing materials (Ramirez, A. L. B. et al. Nat. Chem. 2013, 5, 757-761; Robb, M. J. et al. J. Am. Chem. Soc. 2015, 137, 10946-10949; Zhang, H. et al. Angew. Chem. Int. Ed. 2016, 55, 3040-3044; and Wang, J. et al. ACS Macro Lett. 2015, 834-837, the disclosures of which are incorporated herein by reference), release small molecules (Larsen, M. B. et al. J. Am. Chem. Soc. 2013, 135, 8189-8192; and Diesendruck, C. E. et al. J. Am. Chem. Soc. 2012, 134, 12446-12449, the disclosures of which are incorporated herein by reference), and produce changes in electrical conductivity (Chen, Z. et al. Science 2017, 357, 475-479, the disclosure of which is incorporated herein by reference). Accordingly, continued advancement of this field is highly desirable, as new mechanophore discoveries and development will further expand the repertoire of mechanochemical function and will enable novel applications in organic materials.

SUMMARY OF THE INVENTION

Various embodiments are directed to a mechanically-gated photoswitch including:
a mechanophore comprising a Diels-Alder adduct of a diarylethene and a dienophile, wherein the mechanophore is characterized by an ability to undergo a retro [4+2] cycloaddition reaction upon application of a mechanical force to re-produce the diarylethene and the dienophile; and wherein
the diarylethene comprises at least a cyclic diene moiety and two aryl moieties, each attached to each end of one of two carbon-carbon double bonds of the cyclic diene moiety; wherein
the mechanophore is embedded into a polymer, such that at least one chain of the polymer is covalently attached to a part of the Diels-Alder adduct corresponding to the diarylethene, and at least one additional chain of the polymer is covalently attached to a part of the Diels-Alder adduct corresponding to the dienophile; and wherein
the diarylethene is characterized by an ability to accomplish a switch between a ring opened and a ring closed state upon irradiation with light.

In various such embodiments, the switch between the ring opened and the ring closed state is accompanied by a change in spectral properties.

In still various such embodiments, the cyclic diene moiety comprises at least one X, wherein each of the at least one X is a substituted or unsubstituted chemical element independently selected from the group comprising of: $CR_2$, O, S, NR; and wherein R is a functionality further independently selected from the group comprising of: H, halogen, alkyl, alkoxy, alkylamine, aryl, heteroaryl, carbonyl, alkenyl, and any combination thereof.

In yet various such embodiments, the cyclic diene moiety is a cyclopentadiene or a heterocyclic pentadiene.

In still yet various such embodiments, the cyclic diene moiety is further substituted at any available position around its ring with at least one functionality $R_{cd}$, wherein each of the at least one $R_{cd}$ is independently selected from the group consisting of: H, halogen, alkyl, aryl, heteroaryl, alkoxy, alkylamine, alkenyl, carbonyl, a polymer chain of any composition, and any combination thereof.

In various such embodiments, the two aryl moieties are each independently selected from the group consisting of: a substituted or unsubstituted aryl; a substituted or unsubstituted heteroaryl, including thienyl.

In still various such embodiments, the two aryl moieties are the same aromatic moiety.

In still yet various such embodiments, the dienophile is a substituted alkene, substituted with at least one functionality $R_{dp}$, wherein each of the at least one $R_{dp}$ is independently selected from the group consisting of: H, halogen, alkyl, aryl, heteroaryl, alkoxy, alkylamine, carbonyl, alkenyl, a polymer chain of any composition, and any combination thereof.

In yet various such embodiments, the dienophile is a substituted alkene selected from the group consisting of: a maleimide, an acrylate, a methacrylate, a maleate, a fumarate, and any other similarly substituted alkene.

In various such embodiments, the at least one chain of the polymer and the at least one additional chain of the polymer embedding the mechanophore are of approximately similar length.

In still various such embodiments, the polymer comprises a polymeric network of chains.

In still yet various such embodiments, the polymer is selected from the group consisting of: polymethacrylate, polyacrylate, silicone, polyether, polyurethane, polycarbonate, polystyrene, and any combination thereof.

In still various such embodiments, the spectral properties is absorption of light comprising a visible wavelength.

In yet various such embodiments, the switch between the ring opened and the ring closed state is reversible upon exposure to light and at least one other stimulus.

In yet still various such embodiments, the at least one other stimulus is selected from the group consisting of: visible light, light of another wavelength, thermal energy, and any combination thereof.

In still various such embodiments, the mechanically-gated photoswitch has the formula:

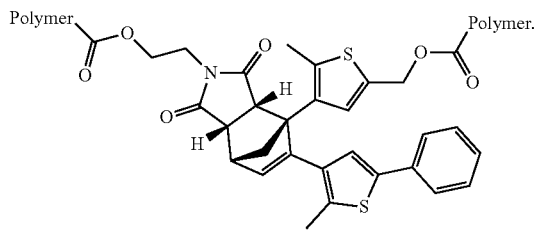

Various other embodiments are directed to a method of mechanochemically-gating a photoswitchable molecular system including:
providing a mechanically-gated photoswitch comprising
 a mechanophore comprising a Diels-Alder adduct of a diarylethene and a dienophile, wherein the mechanophore is characterized by an ability to undergo a retro [4+2] cycloaddition reaction upon application of a mechanical force to re-produce the diarylethene and the dienophile; and wherein
  the diarylethene comprises at least a cyclic diene moiety and two aryl moieties, each attached to each end of one of two carbon-carbon double bonds of the cyclic diene moiety; wherein
the mechanophore is embedded into a polymer, such that at least one chain of the polymer is covalently attached to a part of the Diels-Alder adduct corresponding to the diarylethene, and at least one additional chain of the polymer is covalently attached to a part of the Diels-Alder adduct corresponding to the dienophile; and wherein
the diarylethene is characterized by an ability to accomplish a switch between a ring opened and a ring closed state upon irradiation with light; and
applying the mechanical force to the mechanically-gated photoswitch for a period of time, such that the polymer transduces the mechanical force to the mechanophore and activates the mechanophore to reveal the diarylethene.

In various such embodiments, the switch between the ring opened and the ring closed state is accompanied by a change in spectral properties.

In still various such embodiments, the diarylethene is further irradiated with light to accomplish the switch.

In yet various such embodiments, the switch between the ring opened and the ring closed state is reversible upon exposure to light and at least one other stimulus.

In yet still various such embodiments, the at least one other stimulus is selected from the group consisting of: visible light, light of another wavelength, thermal energy, and any combination thereof.

In various such embodiments, applying the mechanical force comprises deforming the polymer.

In still various such embodiments, deforming the polymer is a method selected from the group consisting of: application of tension, compression, shearing, stretching, grinding, and any combination thereof.

In yet still various such embodiments, the cyclic diene moiety comprises at least one X, wherein each of the at least one X is a substituted or unsubstituted chemical element independently selected from the group comprising of: $CR_2$, O, S, NR; and wherein R is a functionality further independently selected from the group comprising of: H, halogen, alkyl, alkoxy, alkylamine, aryl, heteroaryl, alkenyl, carboxyl, and any combination thereof.

In yet various such embodiments, the cyclic diene moiety is a cyclopentadiene or a heterocyclic pentadiene.

In still various such embodiments, the two aryl moieties are each independently selected from the group consisting of: an substituted or unsubstituted aryl; a substituted or unsubstituted heteroaryl, including thienyl.

Yet various other embodiments are directed to a polymeric material with mechanical stress visualization capabilities including:
a polymer comprising a plurality of covalently embedded mechanically-gated photoswitches, wherein each mechanically-gated photoswitch comprises
 a mechanophore comprising a Diels-Alder adduct of a diarylethene and a dienophile, wherein the mechanophore is characterized by an ability to undergo a retro [4+2] cycloaddition reaction upon application of a mechanical force to re-produce the diarylethene and the dienophile; and wherein
  the diarylethene comprises at least a cyclic diene moiety and two aryl moieties, each attached to each end of one of two carbon-carbon double bonds of the cyclic diene moiety; wherein
the mechanophore is embedded into the polymer, such that at least one chain of the polymer is covalently attached to a part of the Diels-Alder adduct corresponding to the diarylethene, and at least one additional chain of the polymer is covalently attached to a part of the Diels-Alder adduct corresponding to the dienophile; and wherein
the diarylethene is characterized by an ability to accomplish a switch between a ring opened and a ring closed state upon irradiation with light, such that the switch is accompanied by a change in spectral properties.

Still various other embodiments are directed to a method for stress visualization in a material with mechanical stress visualization capabilities including:
providing a polymeric material with mechanical stress visualization capabilities comprising:
a polymer comprising a plurality of covalently embedded mechanically-gated photoswitches, wherein each mechanically-gated photoswitch comprises:
 a mechanophore comprising a Diels-Alder adduct of a diarylethene and a dienophile, wherein the mechanophore is characterized by an ability to undergo a retro [4+2] cycloaddition reaction upon application of a mechanical force to re-produce the diarylethene and the dienophile; and wherein the diarylethene comprises at least a cyclic diene moiety and two aryl moieties, each attached to each end of one of two carbon-carbon double bonds of the cyclic diene moiety; wherein the mechanophore is embedded into the polymer, such that at least one chain of the polymer is covalently attached to a part of the Diels-Alder adduct corresponding to the diarylethene, and at least one additional chain of the polymer is covalently attached to a part of the Diels-Alder adduct corresponding to the dienophile; and wherein the diarylethene is characterized by an ability to accomplish a switch between a ring opened and a ring closed state upon irradiation with light, such that the switch is accompanied by a change in spectral properties;

applying the mechanical force to the polymeric material with mechanical stress visualization capabilities in a pattern for a period of time, such that the polymer transduces the mechanical force to the mechanophores of the plurality of covalently embedded mechanically-gated photoswitches, and activates the mechanophores to reveal the diarylethenes; and irradiating the polymeric material with mechanical stress visualization capabilities with light to accomplish the switch and reveal the pattern.

In various such embodiments, the switch accomplished by the diarylethene is reversible upon exposure to light and at least one other stimulus.

In still various such embodiments, the at least one other stimulus is selected from the group consisting of: visible light, light of another wavelength, thermal energy, and any combination thereof.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which form a part of this disclosure.

BRIEF DESCRIPTION OF THE DRAWINGS

These and other features and advantages of the present invention will be better understood by reference to the following detailed description when considered in conjunction with the accompanying data and figures, wherein:

FIGS. 3A and 3B illustrate DFT calculations (constrained geometries simulate external force (CoGEF) method performed at the B3LYP/6-31G* level of theory) performed to predict the formation of the cyclopentadiene-based DAE and maleimide fragments resulting from the retro [4+2] cycloaddition reaction due to mechanical elongation of the mechanophore of embodiments; wherein FIG. 3A shows structures of the truncated cyclopentadiene-maleimide mechanophore at various points of elongation, and FIG. 3B shows the calculation of the scission force and the corresponding calculated scission products structures, in accordance with embodiments of the invention.

FIG. 5D shows the analysis behind the optimization of the UV irradiation time length necessary for photoswitching of the DAE obtained from mechanochemical activation of 1; FIG. 5E provides UV-vis absorption spectra recorded for the mixture of cyclopentadiene isomers containing DAE 5 before (solid trace) and after (dashed trace) exposure to UV light ($\lambda$=311 nm, 25 s) for comparison purposes; FIG. 5F illustrates stability of $DAE_{closed}$ isomer of embodiments in absence of light (at room temperature) by providing UV-Vis absorption spectra of the ultrasonicated (70 mins) and UV light irradiated ($\lambda$=311 nm, 25 s) solution of molecule 1 right before and after a 25 min hold in the dark; and FIG. 5G illustrates reversible photochromism of DAEs of embodiments, all in accordance with embodiments of the invention.

DETAILED DISCLOSURE

Figure 1A:
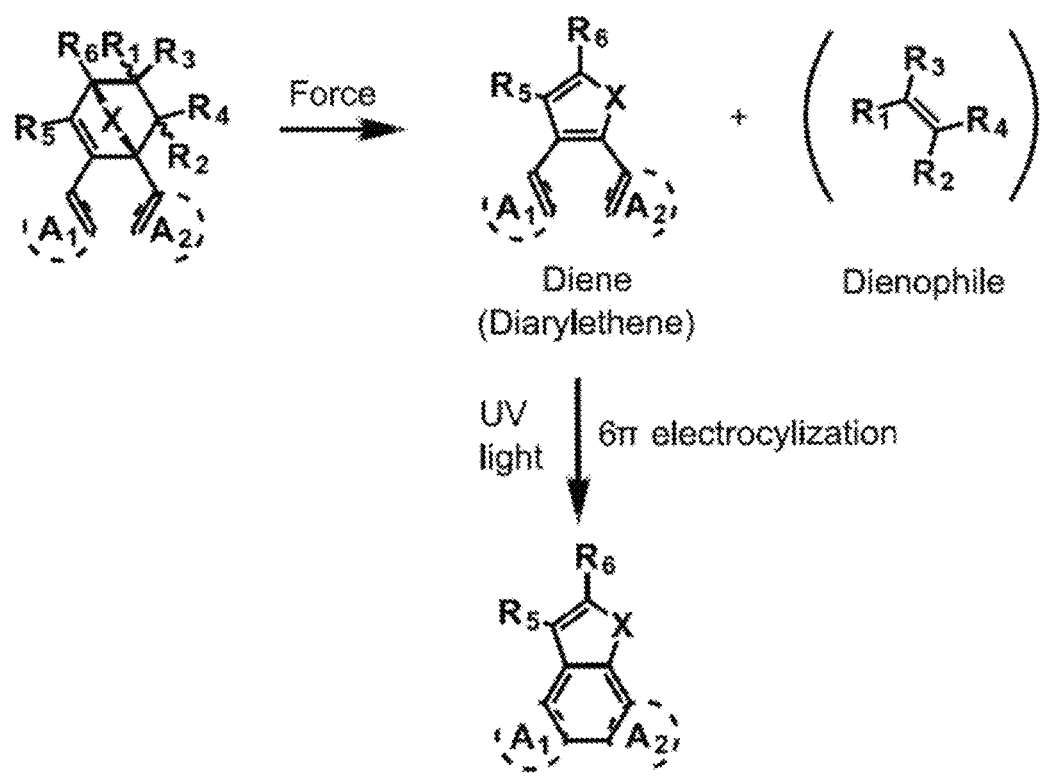
FIG. 1A provides a schematic for the chemical structures of the mechanically-gated photoswitch (left) and the photoswitch resulting from a mechanical actuation thereof (right)

The embodiments of the invention described herein are not intended to be exhaustive or to limit the invention to precise forms disclosed. Rather, the embodiments selected for description have been chosen to enable one skilled in the art to practice the invention.

Turning to the drawings and data, embodiments of new mechanochemically-gated photoswitching molecular systems are provided. In many such embodiments, mechanochemical activation of the mechanically-gated photoswitch, comprising a diarylethene-dienophile Diels Alder adduct mechanophore moiety flanked by polymeric chains or otherwise embedded into a polymeric network, reveals a photochromic diarylethene (DAE) via the retro Diels-Alder reaction. In many embodiments, the mechanochemically generated DAE next undergoes a reversible photoisomerization, wherein it switches between colorless and colored states upon exposure to UV and/or visible light, thus acting as a photoswitch. In many embodiments, the mechanical force alone is responsible for "unlocking" the photochromic properties of the mechanophore, which is otherwise thermally and photochemically stable. In many embodiments, the mechanochemically-gated photoswitches of the instant disclosure may be useful in facilitating applications including, but not limited to: stress sensing, encryption, and patterning in polymeric materials.

The concept of gating in chemistry describes a system in which a desired chemical reaction occurs only if it is preceded by a specific stimulus. Conventionally, this concept has been applied in the context of photoswitching. For example, in a photogated reactivity system, light triggers a chemical change in a molecule to reveal a new structure with unique chemical reactivity (Lemieux, V. et al. *Angew. Chem. Int. Ed.* 2006, 45, 6820-6824; Göstl, R.; Hecht, S. *Angew. Chem. Int. Ed.* 2014, 53, 8784-8787; and Kida, J. et al. *Nat. Commun.* 2018, 9, 3504, the disclosures of which are incorporated herein by reference). Alternatively, in reactivity-gated photoswitching systems (Yokoyama, Y. et al. *Chem. Soc., Chem. Commun.* 1991, 1722-1724, the disclosure of which are incorporated herein by reference), a photoswitchable molecule is revealed after a chemical reaction (Lemieux, V. et al. *Org. Lett.* 2005, 7, 2969-2972; Kühni, J. et al. *Org. Lett.* 2007, 9, 1915-1918; Ohsumi, M. et al. *Chem. Commun.* 2005, 3921-3923; Kawai, S. H. et al. *Eur. J. Org. Chem.* 1999, 1999, 2359-2366; and Irie, M. et al. *J. Am. Chem. Soc.* 1992, 114, 8715-8716, the disclosures of which are incorporated herein by reference).

One type of molecules commonly used in photoswitching applications is diarylethenes (DAEs), which is a class of compounds that have two aromatic groups bonded to each end of a carbon-carbon double bond. The simplest example of a DAE is stilbene. DAEs are an important class of photochromic compounds because they undergo 6n electrocyclic ring-closing reactions upon exposure to UV light to produce fully conjugated and intensely colored species, while visible light triggers the reverse ring-opening reaction to regenerate the original colorless molecules (Irie, M. et al. *Chem. Rev.* 2014, 114, 12174-12277, the disclosure of which is incorporated herein by reference).

Mechanical regulation of photochemical reactivity is promising for a variety of applications ranging from novel lithographic methods to stress-sensing, and to enabling the mechanical history of polymeric materials to be recorded and read on-demand. However, the use of mechanical force in gating (i.e., to regulate a secondary chemical transformation) is an undeveloped area of polymer mechanochemistry. In 2016, Craig and Boulatov reported in Wang, J. et al. *Nat. Commun.* 2016, 7, 13433 (the disclosures of which are incorporated herein by reference) the only prior example of a mechanically-gated chemical reaction, wherein a molecule containing two distinct mechanochemically active groups underwent sequential activation under force (i.e., the second mechanophore unit was gated by the first).

Examples of well-known mechanophores that undergo retro [4+2] cycloaddition reactions under mechanical force include Diels-Alder adducts of maleimide with furan (Stevenson, R. et al. *J. Am. Chem. Soc.* 2017, 139, 16768-16771; and Duan, H.-Y. et al. *Macromolecules* 2017, 50, 1353-1361, the disclosures of which are incorporated herein by reference) and anthracene (Li, J. et al. *J. Am. Chem. Soc.* 2014, 136, 15925-15928; Sung, J. et al. *J. Am. Chem. Soc.* 2018, 140, 5000-5003; and Konda, S. S. M. et al. *J. Am. Chem. Soc.* 2013, 135, 12722-12729, the disclosures of which are incorporated herein by reference). Furthermore, one known way to mechanically activate such mechanophores is to strategically embed them into a polymer chain, placing them in the center of the chain (or, in other words, have them being flanked by two polymer chains of a similar length), and to ultrasonicate the resulting polymer-centered mechanophore in solution, wherein ultrasonication produces the shear forces maximized near the overall polymeric chain midpoint resulting in mechanochemical activation of the mechanophore (as described, for example, in Berkowski, K. L. et al. *Macromolecules* 2005, 38, 8975-8978, the disclosure of which is incorporated herein by reference). In other words, polymer chains judiciously attached to the mechanophore of choice are responsible for transmitting the applied mechanical force to the mechanophore molecule, making it undergo force-induced reactivity and break apart.

This application is directed to embodiments of mechanochemically-gated photoswitching molecular systems and methods for the synthesis and use thereof. In particular, the application is directed to embodiments of a mechanically-gated photoswitch comprising a thermally stable DAE-dienophile Diels-Alder adduct mechanophore embedded into a polymeric chain or network, such that it undergoes the retro [4+2] cycloaddition reaction under mechanical force to reveal a diarylethene (DAE) photoswitch (FIG. 1A). In many embodiments, the DAE-dienophile Diels-Alder adduct is the product of the [4+2] cycloaddition reaction between the diarylethene of many embodiments and a dienophile. In many such embodiments, the diarylethene at least comprises: a cyclic diene moiety, and two aryl moieties ($A_1$ and $A_2$ in FIG. 1A) each attached to each end of one of the two carbon-carbon double bonds of the cyclic diene moiety (FIG. 1A). In many embodiments the cyclic diene is an all carbon cycle. However, in some embodiments, the cyclic diene comprises at least one heteroatom X (FIG. 1A depicts one such example). Therefore, in many embodiments, each of the at least one X is a substituted or unsubstituted chemical element independently selected from, for example, the group comprising: $CR_2$, O, S, NR; and wherein R is a functionality further independently selected from the group comprising: H, halogen, alkyl, alkoxy, alkylamine, aryl, and heteroaryl. In some embodiments, the cyclic diene is cyclopentadiene. In some embodiments, the cyclic diene is further substituted at any available position around the ring. For example, in some embodiments, wherein the cyclic diene is a cyclopentadiene it may be further substituted with one or both functionalities $R_5$ and $R_6$ (FIG. 1A), wherein $R_5$ and $R_6$ are each, independently, selected from the group comprising (but not limited to): H, halogen, alkyl, alkenyl, carbonyl, aryl, heteroaryl, alkoxy, alkylamine, a polymer chain of any composition. In some embodiments, $R_5$ and $R_6$ are the same functionality. In some embodiments, $R_5$ and $R_6$ are interconnected. In many embodiments, either aryl $A_1$ or $A_2$, or both, is a heteroaryl group, such as thienyl. In many embodiments, $A_1$ and $A_2$ are further functionalized as necessary. In some embodiments, $A_1$ and $A_2$ are the same aryl group. In many embodiments the dienophile is any substituted alkene, wherein substituents $R_1$, $R_2$, $R_3$, and $R_4$ are each independently selected from the group comprising (but not limited to): H, halogen, alkyl, alkenyl, aryl, heteroaryl, alkoxy, alkylamine, carbonyl, a polymer chain of any composition. In some embodiments, the dienophile is an alkene selected from the group comprising, but not limited to: an acrylate, methacrylate, maleate, fumarate, and any other similarly substituted alkene. In some embodiments, the dienophile is a maleimide of any substitution.

Figure 1B:
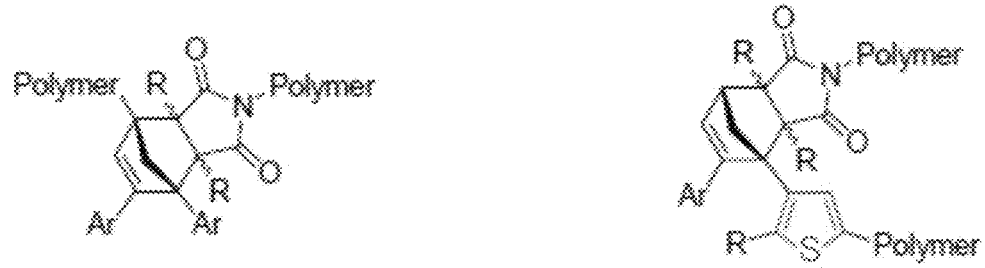
FIG. 1B illustrates various scenarios for the embedding of the mechanophore of the mechanically-gated photoswitch into a polymer; and 1C illustrates the strategy for achieving mechanochemically-gated photoswitching, all in accordance with embodiments of the invention.

In many embodiments, the mechanophore comprising the DAE-dienophile Diels-Alder adduct is covalently embedded into a polymer, such as a single polymer chain or a polymeric network, wherein the attached polymer transmits the applied mechanical force to the mechanophore for activation. In some embodiments, the polymer is selected from, for example, the group comprising: poly(methyl methacrylate) (PMMA), poly(methyl acrylate) (PMA), polydimethylsiloxane (PDMS), poly(ethylene glycol) (PEG), and polyurethane. In many embodiments, the polymer is at least two single chains of an approximately same length flanking the mechanophore such that one chain is attached to the portion corresponding to the dienophile of the Diels-Alder adduct, the other chain is attached to the portion derived from the DAE, and the mechanophore is positioned in the center of the overall construct. In such embodiments, application of external force, such as, for example, provided by ultrasonication, produces tensile forces maximized near the overall chain's midpoint, where the mechanophore is situated, and, thus, promotes mechanophore activation. In some embodiments more than two polymeric chains are attached to the mechanophore, as long as at least one chain is attached to each one—the diene and the dienophile moieties of the Diels-Alder adduct mechanophore of embodiments. In some embodiments, the mechanophore is embedded into a force transmitting polymeric network. In many embodiments, the polymer is attached to the dienophile portion of the Diels-Alder adduct at any available position, including as substituent $R_1$, $R_2$, $R_3$, or $R_4$ (FIG. 1A) or any combination thereof, or any other position, such as, for example at the nitrogen atom of a maleimide dienophile. In many embodiments, the polymer is attached to the DAE derived moiety of the Diels-Alder adduct at any available position, including on the cyclic diene moiety, for example, as substituent $R_5$ or $R_6$, or any combination thereof, in a cyclopentadiene cyclic diene as depicted in FIG. 1B, left; and at either one of the aryl moieties, as, for example, depicted in FIG. 1B right.

Any method of mechanical force application can be used for activation of the mechanophores of embodiments, as long as the force can be transduced to the mechanophore with sufficient energy to induce the retro Diels-Alder reaction within the mechanophore and the mechanophore's breakage. In some embodiments, the mechanical force is provided by means of ultrasonication and is transduced to the Diels-Alder adduct moiety via the mechanophore's polymer chains flanking the Diels-Alder adduct. In some embodiments, the force is transmitted to the mechanophore embedded within a polymeric material via deformation of the polymeric material. In some such embodiments, the methods of deformation may include application of: tension, compression, shearing, stretching, grinding, and any combination thereof.

In many embodiments, the DAE released by the mechanochemical activation of the mechanophore is capable of photoisomerization between the ring opened and ring closed states upon exposure to UV and/or visible light, wherein such switching is accompanied by a change in spectral properties. In many embodiments, the photoswitching activity of the DAE is reversible upon sequential irradiation with UV and visible light, or with any other photochemical and/or thermal stimulus. In many embodiments, the accompanying spectral changes include visible coloration.

Figure 1C:
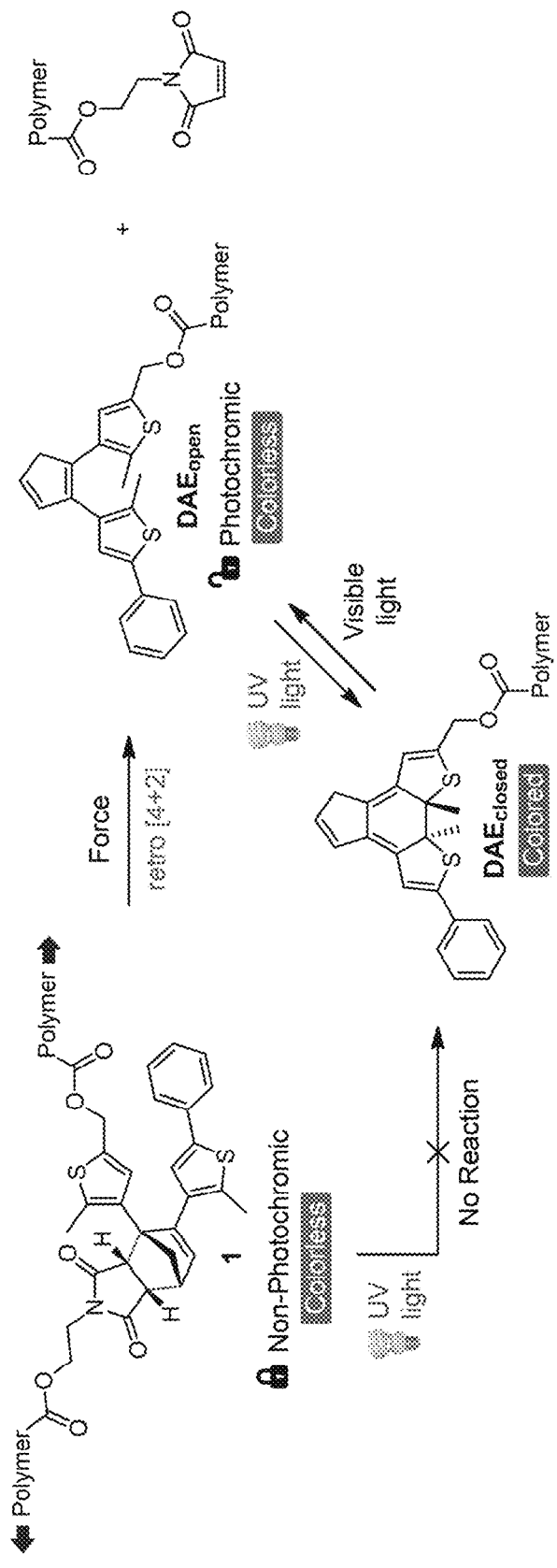

FIG. 1C schematically illustrates the mechanochemically-gated photoswitching system of many embodiments. Here, molecule 1 of embodiments, comprising a mechanophore moiety covalently embedded into a polymer chain in a way that makes the mechanophore susceptible to activation by ultrasound-induced mechanical force, is provided as an example. In many such embodiments, mechanical activation of the cyclopentadiene-maleimide adduct portion of 1 generates the photochromic, colorless $DAE_{open}$ molecule, which can be, in turn, photoisomerized (i.e., switched) back and forth between the colorless ring opened species ($DAE_{open}$) and the colored ring closed species ($DAE_{closed}$) upon sequential exposure to UV light and visible light, respectively. In many embodiments, the mechanophore of the instant disclosure, such as the mechanophore moiety within 1, is photochemically inert because it does not possess the electronic framework necessary for cyclization, which is only revealed after the mechanochemically-induced retro Diels-Alder reaction. In many embodiments, the strategic attachment of polymeric chains to the mechanophore (e.g., as in 1) facilitates and guides the application of the external mechanical stress to induce the retro [4+2] (Diels-Alder) cycloaddition reaction of the mechanophore of embodiments and, thus, to achieve the desired mechanochemical gating action. In some embodiments, the polymer chains flanking the mechanophore moiety of the application are of an approximately same length and allow for facile mechanical actuation of the mechanophore via ultrasonication of its solution, wherein ultrasonication produces forces maximized near the overall chain's midpoint where the mechanophore is located. However, in other embodiments other methods of force application are employed. For example, in some embodiments, force is transmitted to the mechanophore embedded into a polymeric material under one of: tension, compression, shearing, stretching, grinding, and any combination thereof.

Figure 2:
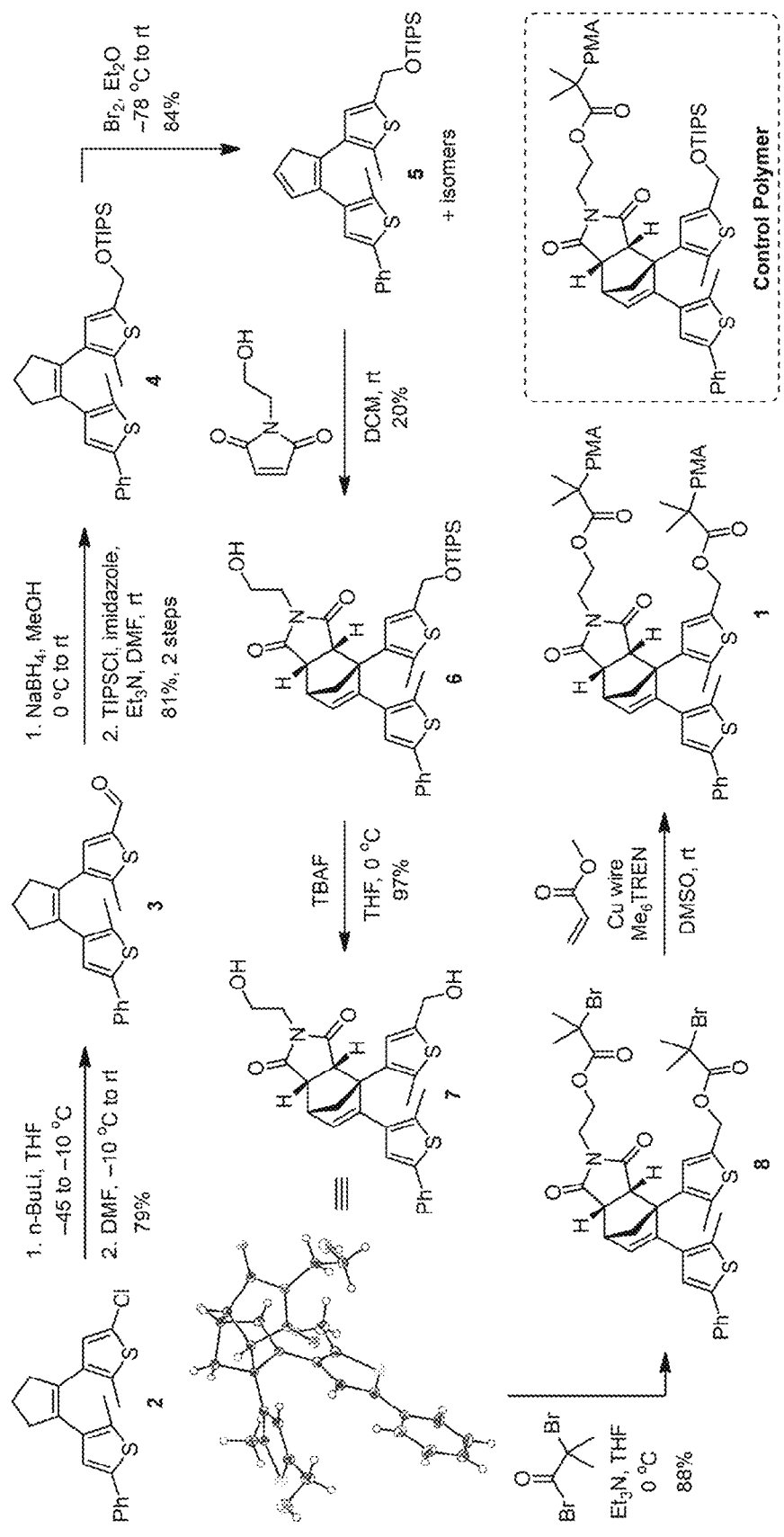
FIG. 2 provides a scheme for the synthesis of exemplary mechanically-gated photoswitch 1 (comprising a cyclopentadiene-maleimide adduct centered on a poly(methyl acrylate) (PMA) chain) and the corresponding Control Polymer in accordance with embodiments of the invention.

FIG. 2 provides an example of a synthetic route for the synthesis of 1 of many embodiments. In many such embodiments, the cyclopentadiene-maleimide adduct is first synthesized from, for example, DAE molecule 2 of FIG. 2 (as seen in Kobatake, S.; et al. Chem. Commun. 2007, 1698-1700, the disclosure of which is incorporated herein by reference). In many such embodiments, a formylation of 2 followed by a two-step reduction and protection sequence affords 4, which is next oxidized using bromine in diethyl ether to provide DAE 5, as a mixture of cyclopentadiene tautomers, including the 1,2-disubstituted isomer. Furthermore, in many embodiments, the mixture of isomers 5 may be reacted with N-(2-hydroxyethyl)maleimide in dichloromethane at room temperature to provide a separable mixture of isomeric Diels-Alder adducts, including the desired norbornene imide 6 (i.e., the Diels-Alder adduct mechanophore of embodiments). Here, it should be noted that two of the 5-maleimide adducts afford the norbornene imide mechanophore architectures with a 2,3-diaryl substituted olefin of many embodiments, wherein these two adducts differ in the regiochemistry of the thienyl substituents relative to the diene/maleimide junction, i.e., TIPS protected hydroxymethyl-substituted thiophene can be located either alpha (proximal) or beta (distal) to the diene/maleimide junction. However, according to many embodiments, isomer 6 (and 7) with the proximal geometry and endo configuration (as confirmed by single crystal X-ray diffraction) is expected to have an enhanced mechanochemical reactivity, based on the studies conducted with analogous furan-maleimide adducts having a proximal pulling geometry (as reported in Stevenson and De Bo, JACS 2017, 139, 16768, the disclosure of which is incorporated herein by reference). In many embodiments, esterification of 7 with α-bromoisobutyryl bromide furnishes bifunctional initiator 8, which, subsequently, may be employed in the controlled radical polymerization of, for example, methyl acrylate using Cu wire/Me$_6$TREN in DMSO to afford the poly (methyl acrylate) (PMA) polymer portion of 1, such that the cyclopentadiene-maleimide adduct is positioned near the center of the overall polymer chain for most efficient activation by ultrasonication. However, it should be noted that, in many embodiments, polymer chains and polymer networks of any suitable composition for the application at hand can be used with the mechanophores of embodiments, as long as such polymeric material is effective at transducing the applied mechanical force to the mechanophore. Furthermore, the installation of the polymeric component may be conducted as a part of the overall mechanophore's synthesis, or as a separate post-synthetic step. In addition, the sequence of the synthetic steps presented in FIG. 2 can be adjusted to produce Control Polymer of embodiments, wherein the norbornene imide moiety caps the polymer chain on one end, rather than is placed in the chain's center. For example, Control Polymer ($M_n$=93 kg/mol; Đ=1.08) may be synthesized by starting from TIPS-protected Diels-Alder adduct 6 with a single hydroxyl group. Such Control Polymer of embodiments is expected to be inert to mechanical actuation by ultrasonication and can be used to elucidate and probe the properties and activation of polymer-embedded mechanophores of some embodiments.

Figure 3A:
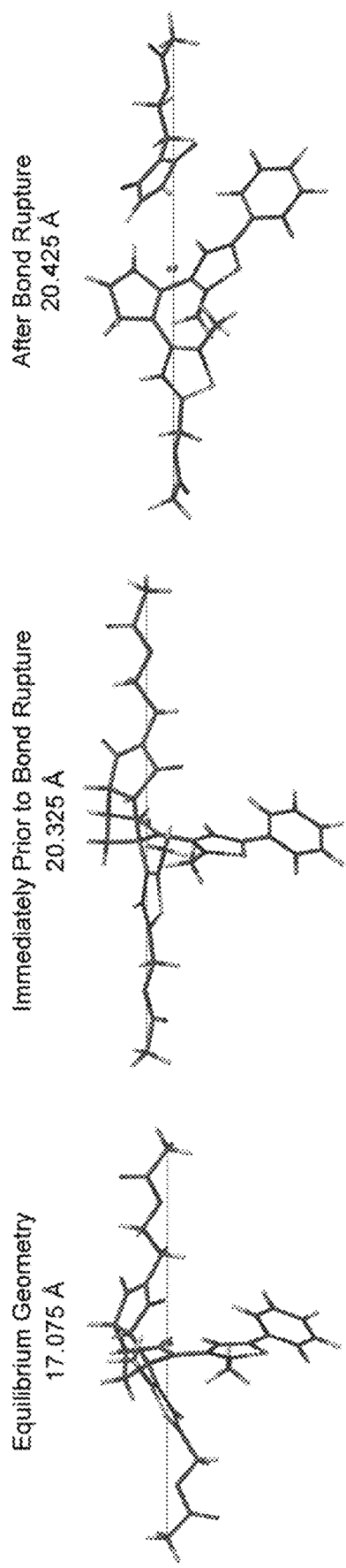
Figure 3B:
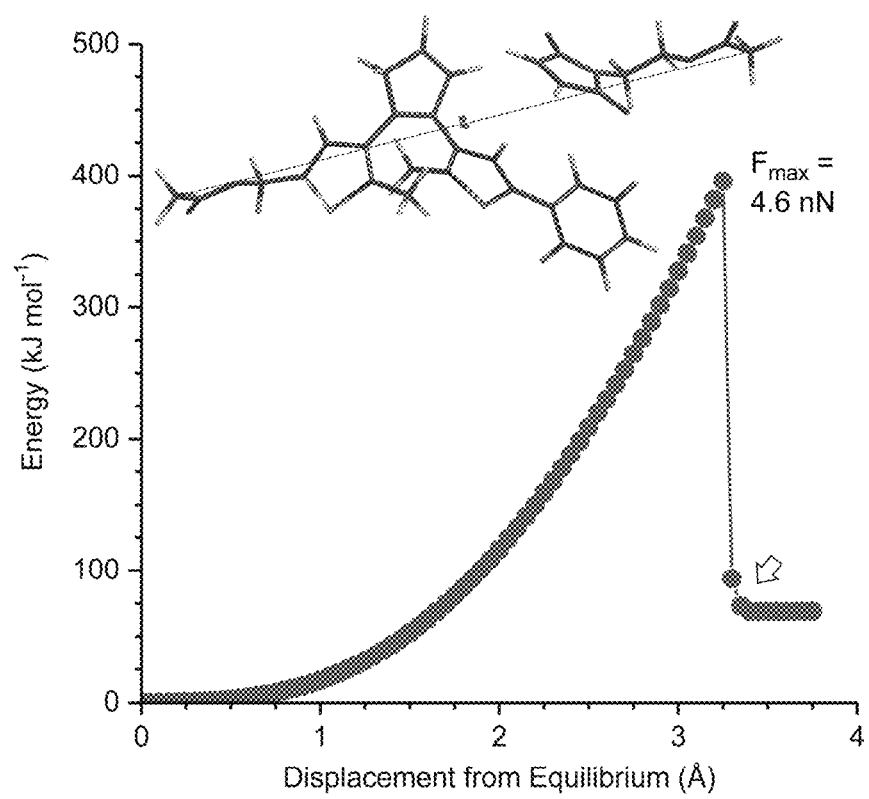

FIGS. 3A and 3B illustrate density functional theory (DFT) calculations performed to evaluate the mechanochemical activity of cyclopentadiene-maleimide adduct mechanophore of 1 exemplary of many embodiments, wherein the calculations use the constrained geometries simulate external force (CoGEF) technique (as described in, for example: Beyer, M. K. *J. Chem. Phys.* 2000, 112, 7307-7312; and Kryger, M. J.; et al. *J. Am. Chem. Soc.* 2011, 133, 18992-18998, the disclosures of which are incorporated herein by reference) performed at the B3LYP/6-31G* level of DFT. For these calculations, starting from the equilibrium geometry of a truncated structure with terminal acetyl groups, the distance between methyl carbon atoms was increased in increments of 0.05 Å and the energy of the molecule was minimized at each step (as depicted in FIG. 3A). Although not to be bound by theory, the computational results indicate that the mechanical elongation of the DAE-dienophile adducts of embodiments induces a retro Diels-Alder reaction to generate the cyclic diene-based DAE and the dienophile fragments. In the example afforded by 1, the calculations presented in FIG. 3B estimate that, for 1, this reaction occurs with a rupture force of approximately 4.6 nN, which is comparable to many other putative mechanophores including furan-maleimide Diels-Alder adducts, and falls within the force maxima range of 2.0 nN to 5.9 nN generally expected for mechanophores predicted by this method of calculation.

Figure 4:
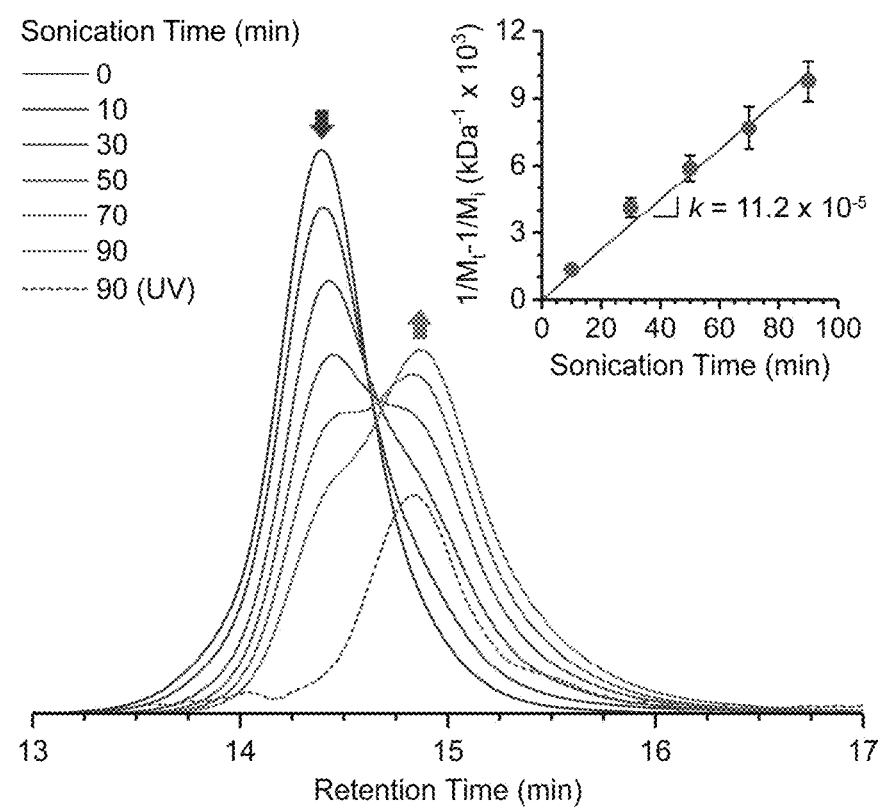
FIG. 4 provides various data collected from the Gel Permeation Chromatography (GPC) monitoring of ultrasonication of 1 over a period of 90 minutes, including: 1) GPC traces obtained with a refractive index (RI) detector (solid lines) for solution samples of polymer 1 taken at various ultrasonication times, which show that ultrasound-induced mechanochemical activation of 1 causes chain scission near the polymer midpoint, resulting in attenuation of the initial polymer peak and an increase in a new peak at approximately one-half of the original $M_n$; 2) a GPC trace obtained using a UV-vis detector monitored at 460-550 nm (dashed trace) for a sample of 1 subjected to ultrasonication for 90 min and then irradiated with UV light ($\lambda$=311 nm, 60 s) immediately prior to the analysis, which demonstrates the generation of a photochromic moiety covalently bound to the polymer's half fragment; and 3) analysis to determine the rate constant of the mechanophore's polymer chain scission (inset), wherein error bars represent standard deviation, all in accordance with embodiments of the invention.

In many embodiments, application of mechanical force, such as, for example, produced by ultrasonication, induces mechanochemical activation of the mechanophore of embodiments and reveals the photoactive DAE. As one example, FIG. 4 provides a GPC analysis of mechanochemical activity of the cyclopentadiene-maleimide Diels-Alder adduct 1 of embodiments resulting from pulsed ultrasonication (1 s on/2 s off, 11.0 W/cm$^2$) in THF at 0° C. Here, molecular weights of ultrasonication products are measured by GPC equipped with a multi-angle light scattering detector as a function of time exposed to ultrasonication. In this example, 1 exhibits a steady change in $M_n$ over 90 min of sonication time, decreasing from 90 kg/mol ($M_i$) to a roughly half value of 48 kg/mol. Furthermore, the GPC with a refractive index (RI) detector clearly illustrates (FIG. 4, solid traces) the attenuation of the initial polymer peak ($M_p$=92 kg/mol) with the generation of a new, well-defined peak ($M_p$=51 kg/mol) at approximately one-half the original molecular weight as expected for site-selective cleavage of the cyclopentadiene-maleimide adduct located near the center of the polymer chain. In the example provided by 1, the average rate constant for the polymer chain scission of 1, k', is approximately 11.2×10$^{-5}$ kDa$^{-1}$ min$^{-1}$ (FIG. 4, inset), as calculated using the specific method for the ultrasonication conditions described herein. Additional GPC measurements using a UV-vis detector conducted with the solution of 1 after 90 minute ultrasonication provide further insight into the photochemical properties of the activated mechanophore polymers of embodiments. For example, irradiation of the ultrasonicated solutions of 1 with UV light (λ=311 nm) immediately prior to the UV-vis GPC (monitored at 460-550 nm (vide infra)) reveals a new peak (red dashed trace in FIG. 4), which coincides with the RI traces for the low molecular weight fragment peak (i.e., halved polymer chains), confirming that a polymer-bound photochromic moiety is produced upon chain scission according to many embodiments.

Figure 5A:
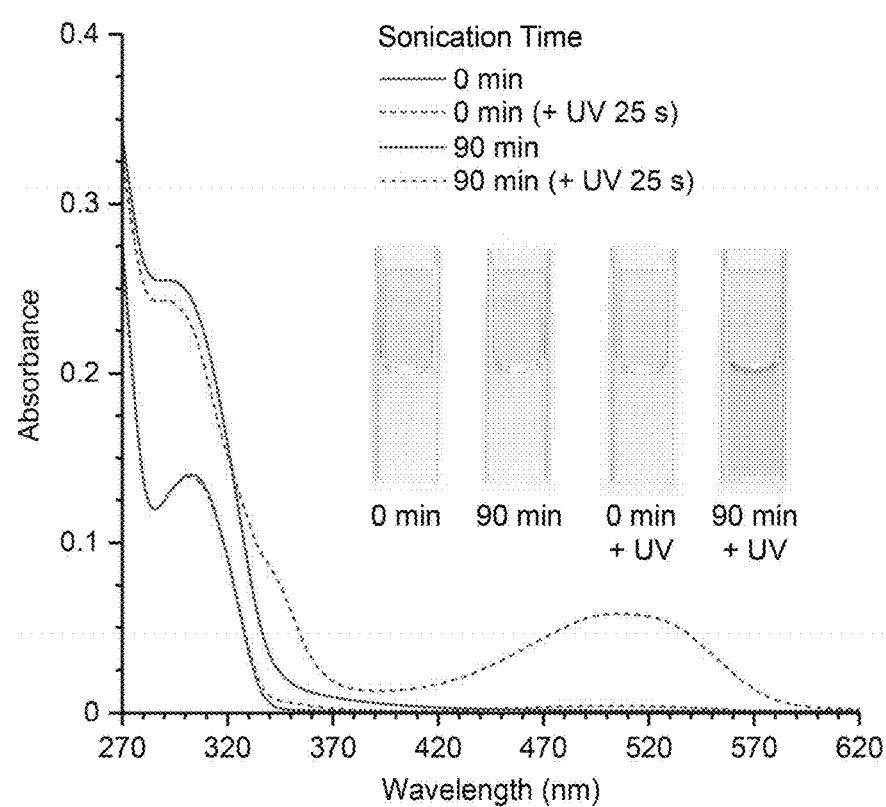
FIGS. 5A through 5G illustrate UV-vis analysis of the mechanochemically-gated photoswitching capabilities of the mechanophore of molecule 1, wherein FIGS. 5A-5C provide UV-vis absorption spectra (accompanied by color photographs) recorded for 1 before, during, and after ultrasonication without (solid traces) and with (dashed traces) UV irradiation ($\lambda$=311 nm, 25 s)
Figure 5B:
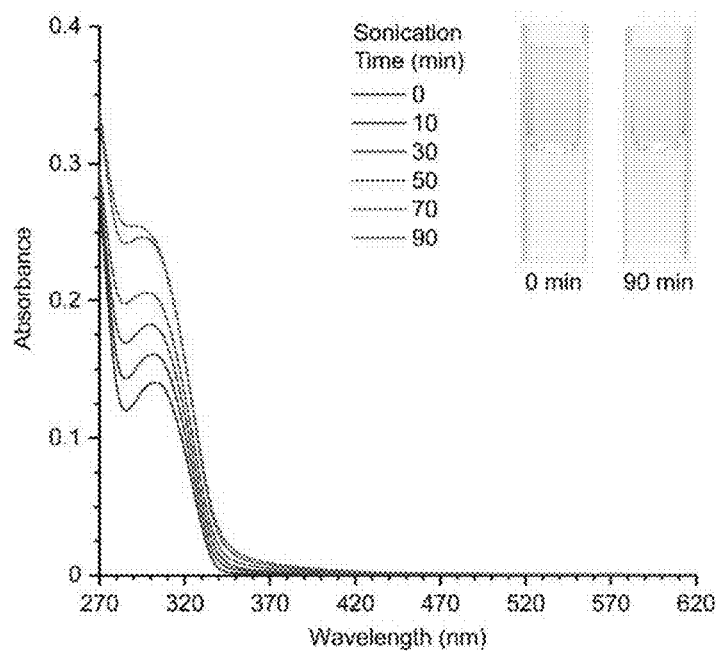
Figure 5C:
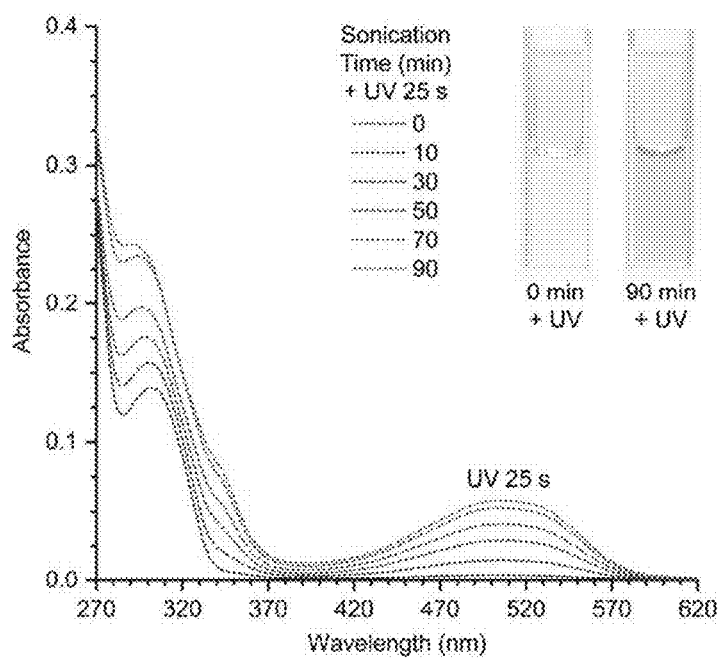
Figure 5D:
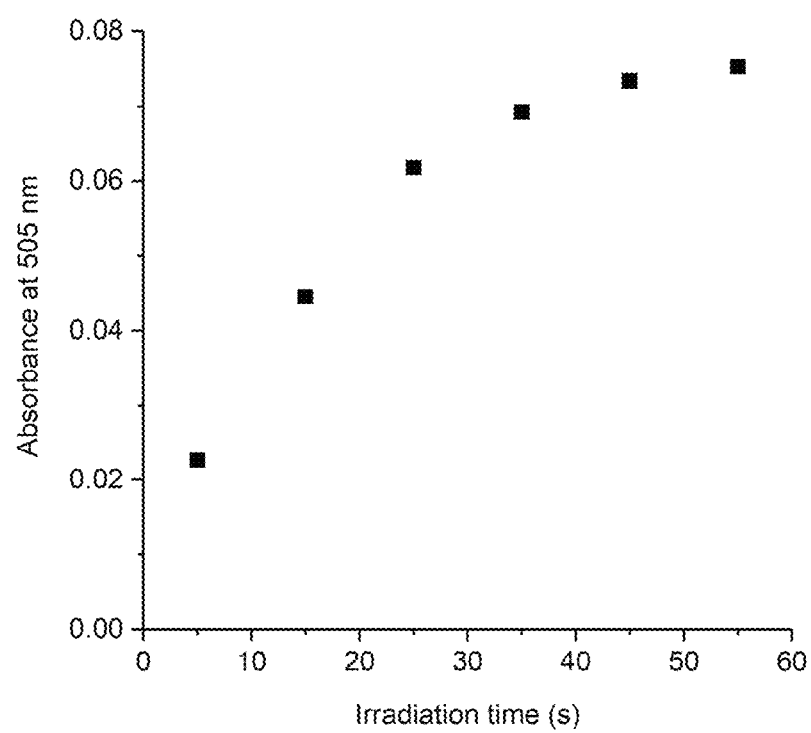

In many embodiments, the applied mechanical force, such as, for example, produced by ultrasound, breaks up the polymer embedded mechanophore moiety of embodiments to reveal the previously latent diarylethene (DAE) that photoisomerizes under UV light, thus accomplishing the mechanochemically-gated photoswitching. For example, FIGS. 5A through 5G illustrate the photochemical changes that accompany the mechanochemical chain scission of 1 of embodiments, as analyzed by UV-vis spectroscopy. For this analysis, absorption spectra for aliquots of the solution of 1 drawn during the ultrasonication at 0, 10, 30, 50, 70, and 90 min intervals were recorded. In many embodiments, the solution of 1 has the peak absorbance in the region of 290-310 nm, which increases in intensity with increasing ultrasonication time (FIGS. 5A-5C), indicating the generation of the DAE moiety. In such embodiments, the solution originally containing only 1 remains colorless throughout the duration of the ultrasonication treatment (FIGS. 5A and 5B). However, in many embodiments, irradiation of the ultrasonicated aliquots with UV light leads to visible coloration, while their absorption spectra reveal a new broad peak centered at 505 nm, which also shows an increase in optical density with longer ultrasonication times (FIGS. 5A, 5C, and 5D). Furthermore, as one example, wherein the DAE is derived from 1, 25 s of UV irradiation (λ=311 nm) under the given conditions is sufficient for this DAE to approach the photostationary state, as illustrated by the analysis presented in FIG. 5D, wherein the absorbance of ultrasonicated 1 at 505 nm (corresponding to DAE$_{closed}$) is recorded as a function of UV irradiation time.

Figure 5E:
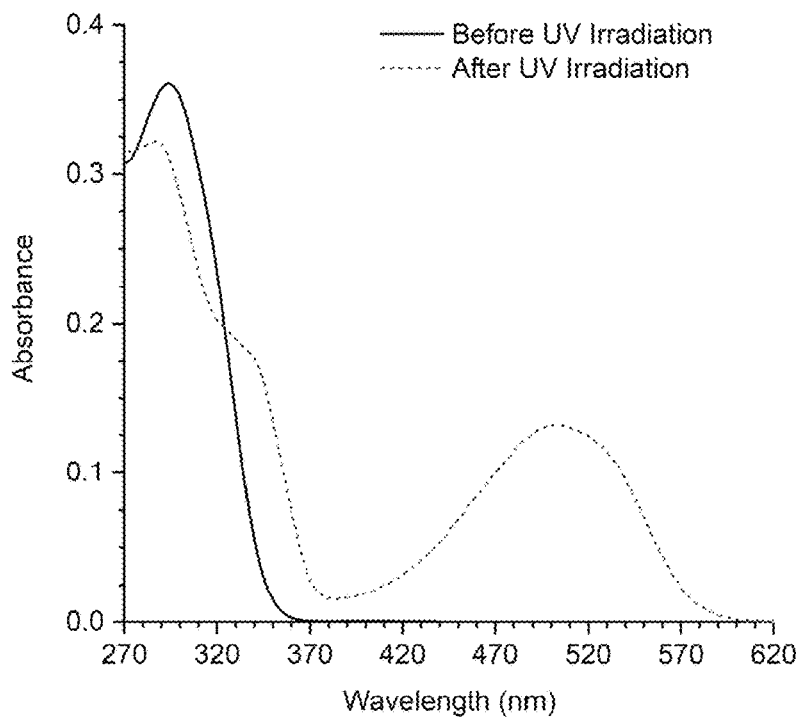
Figure 5F:
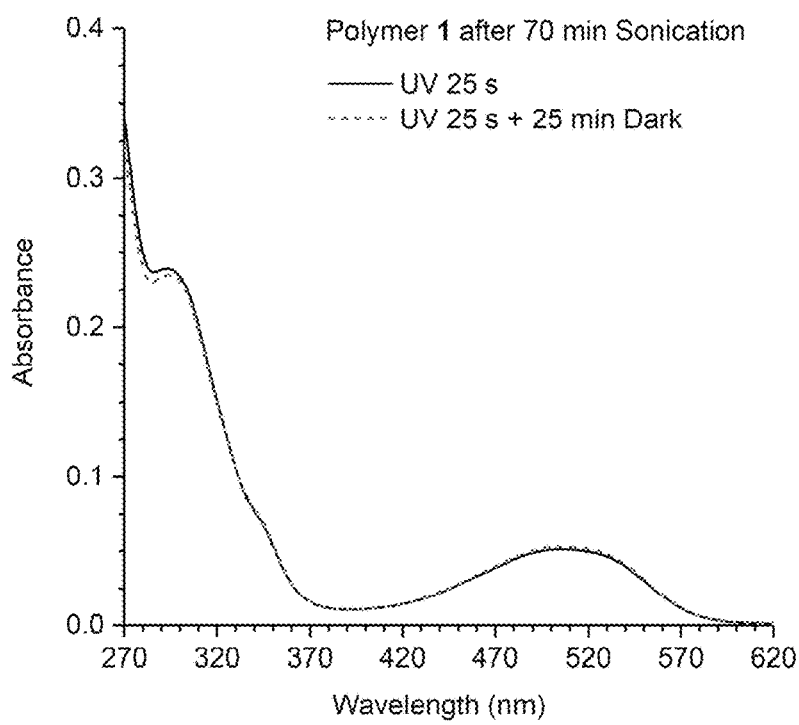

Notably, the photochromic peak observed for ultrasonicated solution of 1 closely matches to the peak found in the absorption spectrum of the ring-closed species generated by UV irradiation of the mixture of cyclopentadiene isomers containing DAE 5 (FIG. 5E). In many embodiments, the spectroscopic changes that accompany the mechanically activated mechanophores of embodiments are also apparent to a naked eye, as their solutions obtain color upon exposure to UV light. For example, the ultrasonicated solution of 1 transforms from colorless to red upon exposure to UV light. However, the specific color of the photoisomerized DAEs of embodiments can vary, depending on the chemical structure of the DAE, such as, for example, the identity and substitution of the cyclic diene comprising the DAE and/or of its aryl groups. Furthermore, in many embodiments, the colored DAE species of embodiments ($DAE_{closed}$) are stable in the dark at ambient temperature, as illustrated by, for example, FIG. 5F, which provides absorption spectra for $DAE_{closed}$ obtained from ultrasonicated and UV-irradiated solution of 1 prior to and after it being kept in the dark for 25 minutes and shows no significant changes in the corresponding spectra.

Figure 5G:
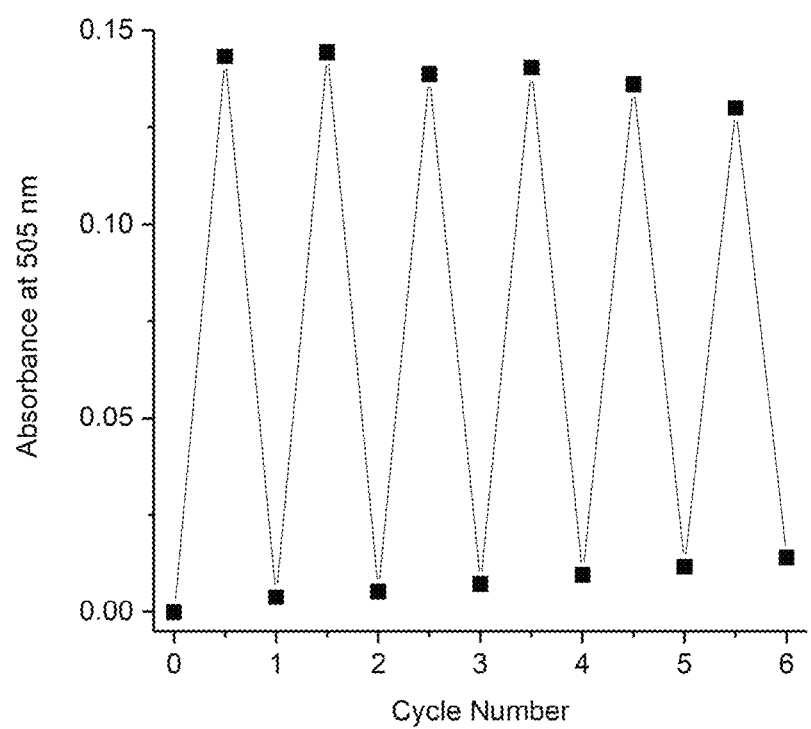

In some embodiments, the photochromic behavior of the mechanophores of the instant disclosure after mechanical activation is reversible by alternating UV and visible light irradiation. For example, the photochromic behavior of 1 after mechanical activation is reversible for at least six cycles with alternating irradiation using UV and visible light as illustrated in FIG. 5G. More specifically, FIG. 5G shows reversible photochromism of the DAE of embodiments obtained from ultrasonication of mechanophore of 1 for 70 min, wherein, in each photoswitching cycle, the sample was first irradiated with UV light for 25 s ($\lambda$=311 nm) to generate the ring-closed DAE isomer, followed by exposure to white light for 2 min to revert to the colorless ring-opened DAE, all while monitoring the absorbance at 505 nm, which corresponds to the absorption maximum of the ring-closed isomer.

Figure 6A:
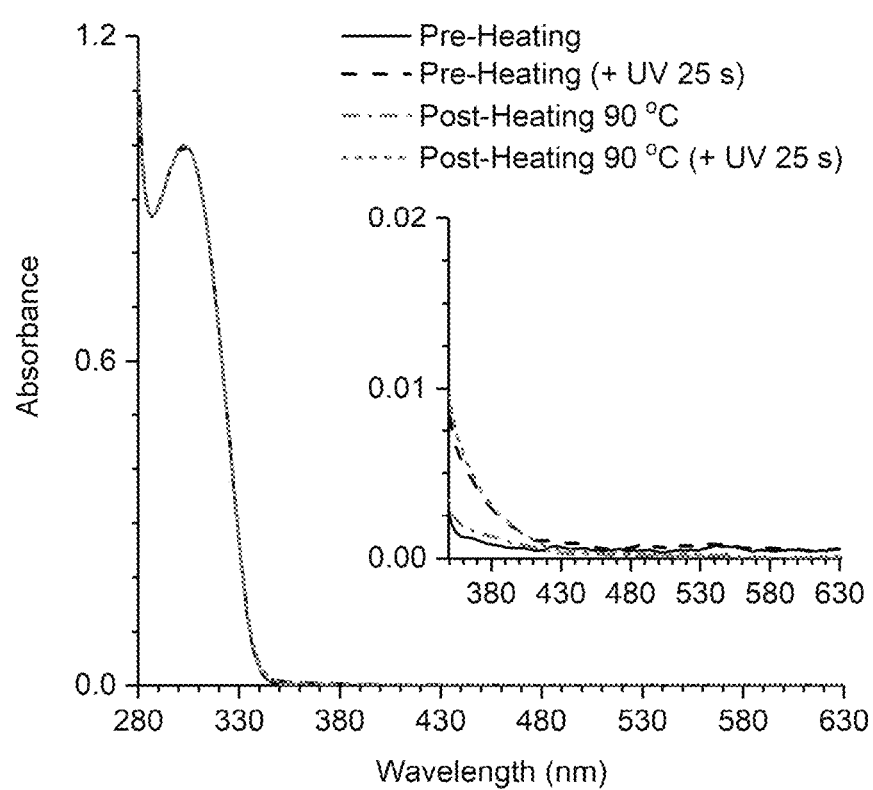
FIGS. 6A and 6B illustrate the thermal stability of cyclopentadiene-maleimide adduct 7 by providing UV-vis absorption spectra recorded for 7 before and after heating it for 3 h at 90° C. in toluene-$d_8$ (FIG. 6A) and the corresponding $^1$H NMR spectra (FIG. 6B), neither of which shows any changes in accordance with embodiments of the invention.
Figure 6B:
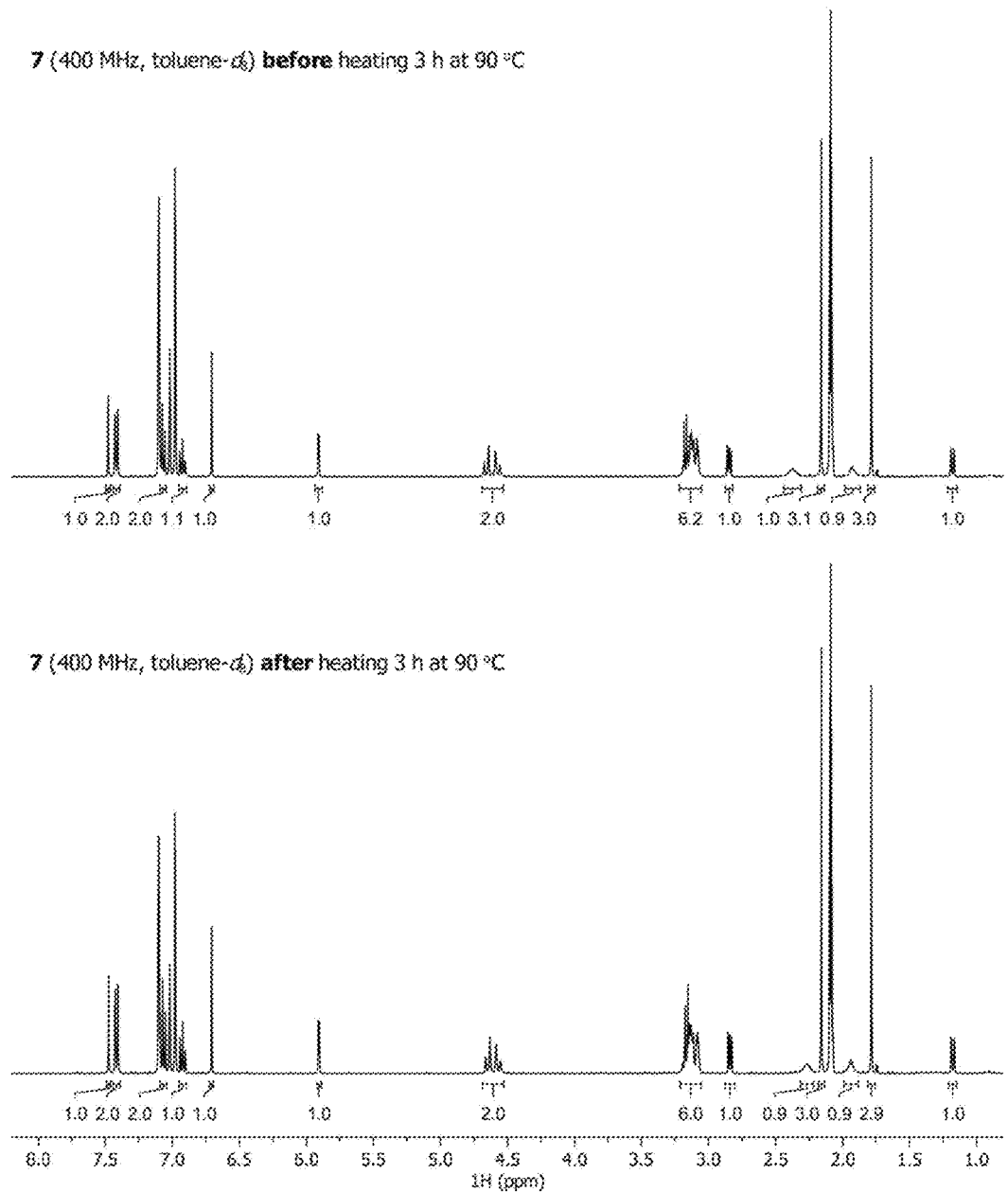

In many embodiments, the mechanophore moieties of the instant application are thermally stable. For example, FIGS. 6A and 6B illustrate the thermal stability of cyclopentadiene-maleimide Diels-Alder adduct 7 (FIG. 2), wherein no spectral or structural changes are observed for the toluene-$d_8$ solution of 7 after heating it for 3 hours at 90° C. (with and without UV irradiation), as evidenced by both UV-vis and $^1$H NMR spectra (FIGS. 6A and 6B, respectively). Although not to be bound by theory, these observations further support the notion of the mechanical activation of the mechanophores of embodiments, wherein the mechanical force, rather than heat or light, is responsible for the changes in the photochemical behavior observed for ultrasonicated mechanophores of the embodiments.

Figure 7:
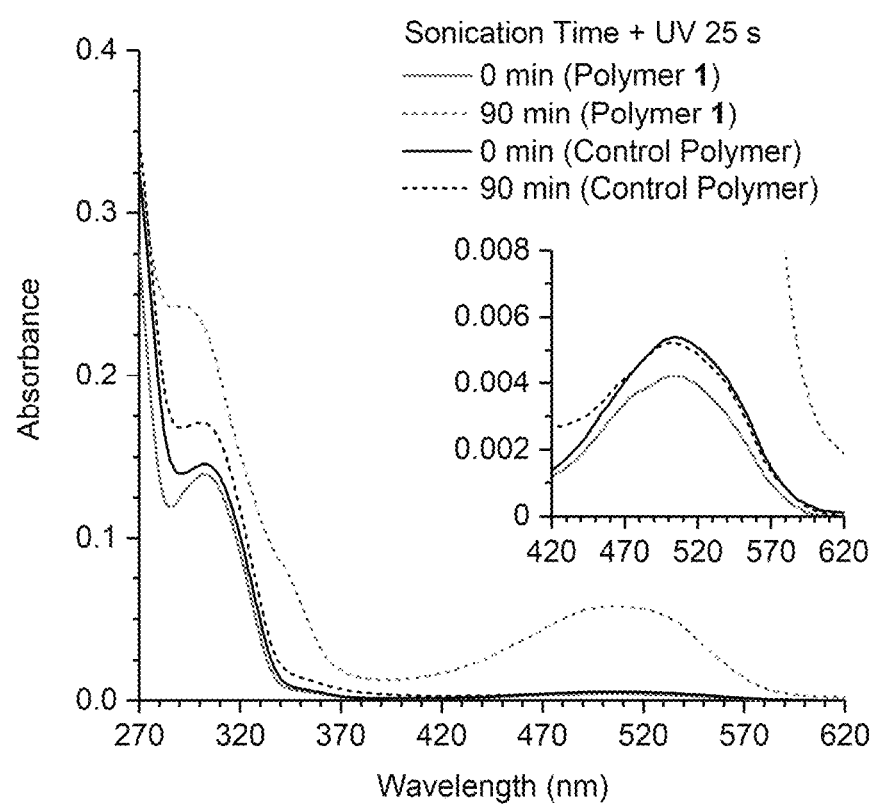
FIG. 7 provides UV-vis absorption spectra recorded for THF solutions of 1 and the corresponding Control Polymer upon exposure to UV irradiation ($\lambda$=311 nm, 25 s) before and after ultrasonication for 90 min, and confirms that Control Polymer is inert toward mechanical stress in accordance with embodiments of the invention.

In addition, the experiments and analysis presented in FIG. 7 further illustrate the mechanical origin of the photochemical transformations observed for the solutions of the mechanophores of embodiments upon ultrasonication. More specifically, FIG. 7 compares UV-vis absorption spectra obtained for THF solutions of 1 and the corresponding Control Polymer, wherein Control Polymer has the same cyclopentadiene-maleimide moiety as 1 but has it attached at one end of the polymeric chain, rather than the chain's center (FIG. 2), upon exposure to UV irradiation ($\lambda$=311 nm, 25 s) before (solid trace) and after (dashed trace) ultrasonication for 90 min. As seen from FIG. 7, in contrast to 1 of embodiments, Control Polymer shows no changes in the absorbance around 505 nm (which corresponds to formation of the DAE of embodiments), regardless of the duration of ultrasonication and exposure to UV light. Notably, both solutions of 1 and Control Polymer display a very weak photochromic peak in the absorption spectrum after UV irradiation but prior to any ultrasonication, however, still, in direct contrast to 1, the corresponding Control Polymer shows no changes in the photochromic properties after ultrasonication (FIG. 7).

Figure 8:
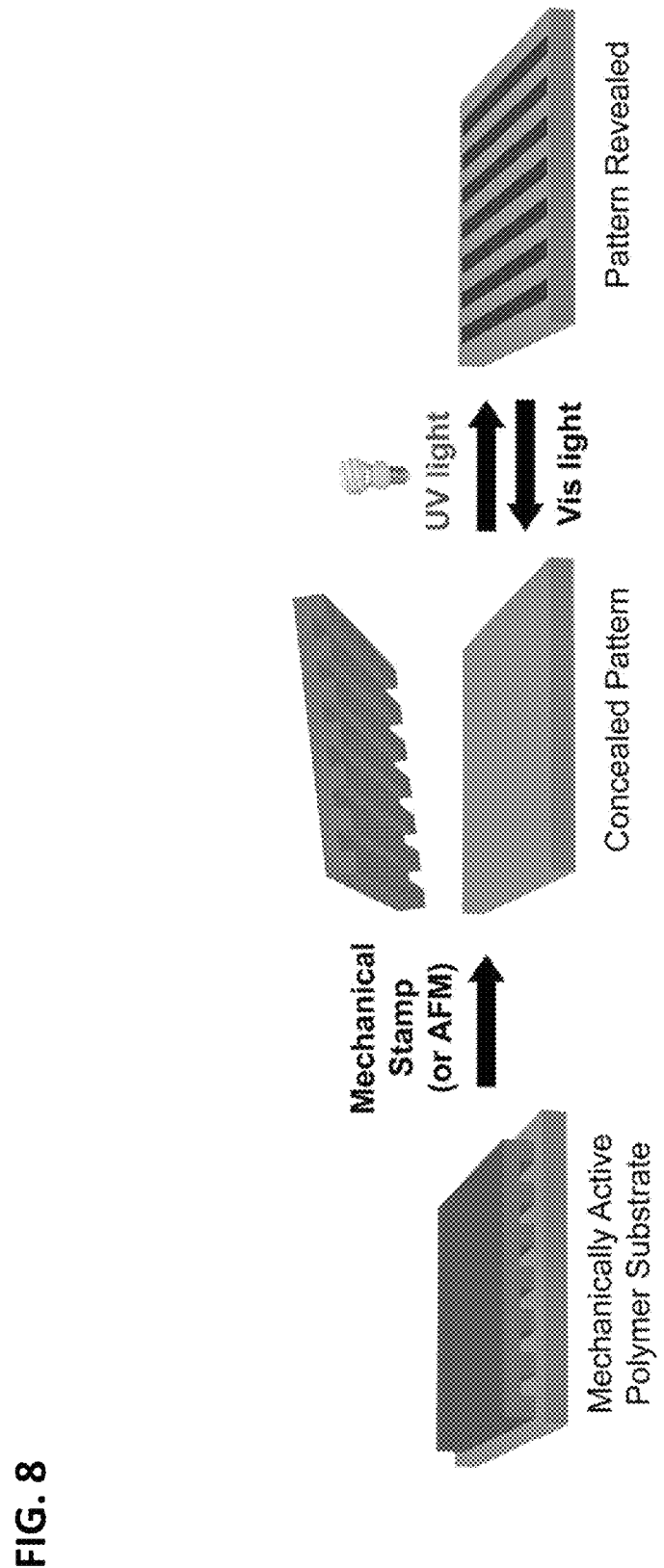
FIG. 8 illustrates use of mechanically-gated photoswitches in polymeric materials for stress-visualization and recording, in accordance with embodiments of the invention.

FIG. 8 illustrates one exemplary application of the mechanically-gated photoswitches of the instant disclosure according to many embodiments. According to such embodiments, the mechanophores described herein allow for new approaches to stress visualization and or stress recording in polymeric materials, wherein the visualization is achieved by first embedding the mechanophores of embodiments into a polymeric substrate of interest; next, using mechanical force to activate the embedded mechanophores; and, subsequently, regulating photochemistry (photoswitching) of the embedded mechanophores. More specifically, in many embodiments, as depicted in FIG. 8, pointedly applying force to certain areas of a polymeric substrate comprising the covalently embedded mechanophores of the instant application (e.g., by applying a mechanical stamp with a desired pattern) activates the mechanophores in those areas and turns them into photoswitches, which, next, can be revealed on demand by UV light irradiation. In some embodiments, the photoswitching can be reversed with another type of a radiation (e.g., visible light) to again conceal the pattern corresponding to the mechanical damage of the polymeric substrate. In many embodiments, such manipulations can be adapted to 1) record the mechanical history of a material (which can be read on-demand thereafter), and 2) enable mechanochemical lithography on polymers (wherein the desired pattern is revealed with light). Notably, a number of molecular mechanochromic mechanophores have been previously demonstrated, wherein such mechanochromic mechanophores directly undergo spectral transformations upon application of mechanical force to signal/reveal stress they undergo (see, for example: Davis, D. A. et al. *Nature* 2009, 459, 68-72; and Robb, M. J. et al. *J. Am. Chem. Soc.* 2016, 138, 12328-12331, the disclosures of which are incorporated herein by reference). However, in stark contrast to the mechanically-gated photoswitches of embodiments, the non-gated systems are susceptible to 1) losing the signal intensity once the stress is removed; and 2) producing non-specific (i.e., non-mechanically-caused) signals due to, for example, extraneous thermal or photochemical stimuli.

EXEMPLARY EMBODIMENTS

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

General Experimental Details

Reagents from commercial sources were used without further purification unless otherwise stated. Methyl acrylate was passed through a short plug of basic alumina to remove inhibitor immediately prior to use. Dry THF, diethyl ether, and DMF were obtained from a Pure Process Technology solvent purification system. All reactions were performed under a N2 or argon atmosphere unless specified otherwise.

Column chromatography was performed on a Biotage Isolera system using SiliCycle SiliaSep HP flash cartridges. NMR spectra were recorded using a Bruker 400 MHz or Varian 500 MHz spectrometer. All $^1$H NMR experiments are reported in δ units, parts per million (ppm), and were measured relative to the signals for residual chloroform (7.26 ppm) or dichloromethane (5.32 ppm) in deuterated solvent. All $^{13}$C NMR spectra were measured in deuterated solvents and are reported in ppm relative to the signals for residual chloroform (77.16 ppm) or dichloromethane (53.84 ppm). High resolution mass spectra (HRMS) were obtained from an Agilent 6200 series time-of-flight mass spectrometer equipped with an Agilent G1978A multimode source (ESI+). Analytical gel permeation chromatography (GPC) was performed using an Agilent 1260 series pump equipped with two Agilent PLgel MIXED-B columns (7.5×300 mm), an Agilent 1200 series diode array detector, a Wyatt 18-angle DAWN HELEOS light scattering detector, and an Optilab rEX differential refractive index detector. The mobile phase was THF at a flow rate of 1 mL/min. Determination of dn/dc was performed online assuming 100% mass elution under the peak of interest. Molecular weights and molecular weight distributions were calculated by light scattering using a dn/dc value of 0.062 mL/g for poly(methyl acrylate). Preparative supercritical fluid chromatography (SFC) separation was conducted using a Jasco 2000 Series Preparative SFC system equipped with a 19×250 mm Waters Viridis Silica 2-EP OBD SFC column using standard 40° C. column compartment temperature and 10.0 MPa back pressure regulator settings. UV-Vis absorption spectra were recorded on a Thermo Scientific Evolution 220 spectrometer. Ultrasound experiments were performed using a Vibra Cell 505 liquid processor equipped with a 0.5-inch diameter solid probe (part #630-0217), sonochemical adapter (part #830-00014), and Suslick reaction vessel (part #830-00011) from Sonics and Materials. UV irradiation was performed using a Philips PL-S 9W/01/2P UVB bulb with a narrow emission between 305-315 nm and a peak at 311 nm under ambient conditions unless indicated otherwise.

SYNTHETIC DETAILS 5-methyl-4-(2-(2-methyl-5-phenylthiophen-3-yl) cyclopent-1-en-1-yl)thiophene-2-carbaldehyde (3)

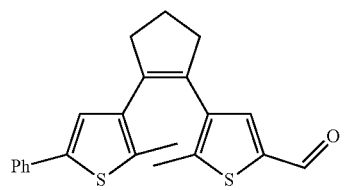

3

A flame-dried round bottom flask equipped with a stir bar was charged with diarylethene 2 (see Kobatake, S. et al. Chem. Commun. 2007, 1698-1700, the disclosure of which is incorporated herein by reference) (816 mg, 2.20 mmol) and sealed with a rubber septum. The flask was evacuated and backfilled with nitrogen (3×) followed by the addition of dry THF (15 mL). The flask was cooled to −45° C., followed by the slow addition of n-butyllithium (2.5 M in hexanes, 0.98 mL, 2.4 mmol). The reaction was allowed to warm to −10° C. over 30 min, after which it was maintained between −20° C. and −10° C. for another 30 min. Dry DMF (0.56 mL, 7.2 mmol) was then added and the flask was allowed to warm to room temperature. After stirring for 4 h, the reaction mixture was poured into aqueous NH$_4$Cl (10%, 50 mL) and extracted with EtOAc (50 mL). The organic phase was washed with brine (50 mL), dried over MgSO$_4$, filtered, and concentrated under reduced pressure. The crude product was purified by column chromatography (5-40% EtOAC/hexanes) to provide the title compound as a light brown viscous liquid (630 mg, 79%). R$_f$=0.51 (EtOAc:hexane 1:1). $^1$H NMR (400 MHz, CDCl$_3$) δ: 9.76 (s, 1H), 7.53-7.48 (m, 3H), 7.39-7.33 (m, 2H), 7.28-7.22 (m, 1H), 7.01 (s, 1H), 2.91-2.80 (m, 4H), 2.13 (p, J=7.4 Hz, 2H), 2.11 (s, 3H), 1.98 (s, 3H) ppm. $^{13}$C{$^1$H} NMR (100 MHz, CDCl$_3$) δ: 13.9, 14.9, 22.6, 37.9, 38.1, 123.2, 124.8, 126.8, 128.4, 132.7, 133.7, 133.9, 135.7, 135.9, 137.3, 137.7, 139.5, 139.8, 145.9, 181.9 ppm. HRMS (ESI, m/z): calcd for [C$_{22}$H$_{21}$OS$_2$]$^+$ (M+H)$^+$, 365.1028; found, 365.1027.

Triisopropyl((5-methyl-4-(2-(2-methyl-5-phenylthiophen-3-yl)cyclopent-1-en-1-yl)thiophen-2-yl) methoxy)silane (4)

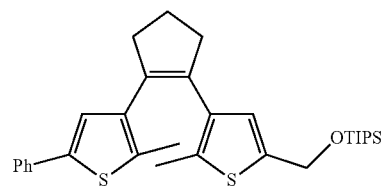

4

A round bottom flask equipped with a stir bar was charged with methanol (14 mL) and cooled to 0° C. in an ice bath followed by the addition of sodium borohydride (0.60 g, 16 mmol) in three portions. Diarylethene 3 (1.00 g, 2.74 mmol) was dissolved in THF (7 mL) and added dropwise to the cooled solution. The flask was sealed with a rubber septum, purged with nitrogen, and allowed to warm to room temperature. After 12 h, the reaction was poured into aqueous ammonium chloride (10%, 20 mL) and extracted with diethyl ether (50 mL). The organic layer was washed with brine (50 mL), dried over MgSO$_4$, and concentrated under reduced pressure. Without further purification, the alcohol was dissolved in anhydrous DMF (6 mL) in a flame-dried round bottom flask equipped with a stir bar under a nitrogen atmosphere. Triethylamine (0.50 mL, 3.6 mmol), imidazole (50 mg, 0.73 mmol), and triisopropylsilyl chloride (TIPSCl, 0.80 mL, 3.7 mmol) were added under a blanket of nitrogen and the reaction was stirred at room temperature. After 20 h, the solution was poured into aqueous ammonium chloride (10%, 50 mL) and extracted with diethyl ether (50 mL). The organic layer was washed with brine, dried over MgSO$_4$, and concentrated under reduced pressure. The crude product was purified by column chromatography (0-10% DCM/hexanes) yielding the title compound as a light pink sticky solid (1.16 g, 81%). R$_f$=0.71 (EtOAc:hexanes 1:20). $^1$H NMR (400 MHz, CDCl$_3$) δ: 7.51-7.43 (m, 2H), 7.35-7.30 (m, 2H), 7.24-7.18 (m, 1H), 7.01 (s, 1H), 6.60 (s, 1H), 4.82 (s, 2H), 2.86-2.74 (m, 4H), 2.05 (tt, J=8.0, 6.9 Hz, 2H), 1.96 (s, 6H), 1.20-1.09 (m, 3H), 1.10-1.01 (m, 18H) ppm. $^{13}$C{$^1$H} NMR (100 MHz, CDCl$_3$) δ 12.2, 14.49, 14.53, 18.2, 23.1, 38.57, 38.60, 61.3, 124.2, 124.5, 125.4, 127.0, 128.9, 133.8, 134.1, 134.5, 134.7, 134.9, 135.1, 136.9, 139.6, 141.1 ppm. HRMS (ESI, m/z): calcd for [C$_{31}$H$_{42}$OS$_2$Si]$^+$ (M+NH$_4$)$^+$, 540.2785; found, 540.2773.

Triisopropyl((5-methyl-4-(2-(2-methyl-5-phenylthi-ophen-3-yl)cyclopenta-1,3-dien-1-yl)thiophen-2-yl)methoxy)silane (5, and Isomers)

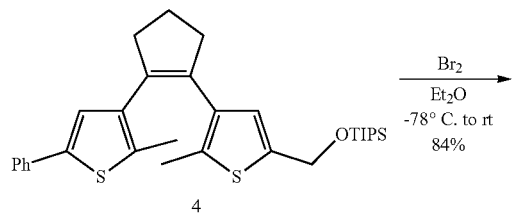

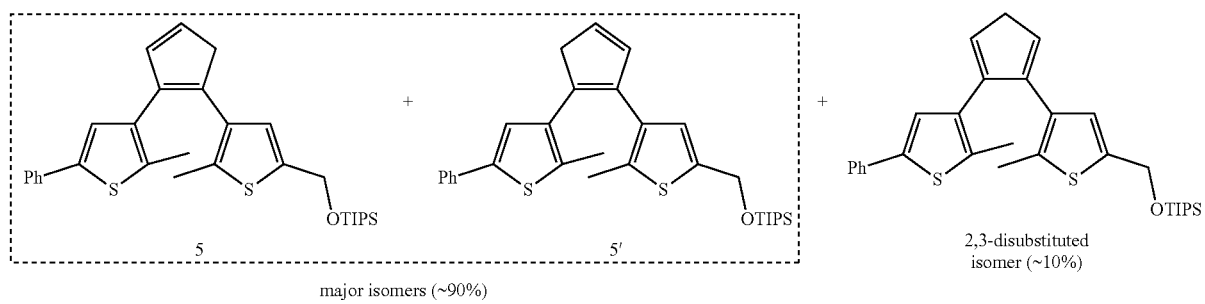

Diarylethene 4 (1.68 g, 3.23 mmol) was dissolved in anhydrous diethyl ether (300 mL) in a flame-dried round bottom flask and sealed with a septum. The solution was cooled to −78° C., followed by the dropwise addition of bromine (0.165 mL, 3.22 mmol) in the dark. The reaction was allowed to warm to room temperature over 1 h, then poured into aqueous NaHCO$_3$ (5%, 200 mL). The aqueous layer was removed, and the organic layer was washed with brine (200 mL), dried over MgSO$_4$, and concentrated under reduced pressure. The crude product was purified by column chromatography using hexanes/triethyl amine (99:1 v:v) as the eluent to afford a yellow oil (1.42 g, 84%) which was used without further purification. The isolated mixture contained ~90 mol % 5/5' (1:1) along with ~10 mol % of the 2,3-disubstituted isomer as estimated by $^1$H NMR spectroscopy. R$_f$=0.69 (EtOAc:hexanes 1:19). $^1$H NMR (400 MHz, CDCl$_3$, major) δ: 7.53-7.47 (m, 2H), 7.36-7.30 (m, 2H), 7.25-7.20 (m, 1H), 7.05 (m, 1H), 6.71-6.63 (m, 2H), 6.52-6.47 (m, 1H), 4.84 (s, 2H), 3.46 (t, J=1.6 Hz, 1H), 3.44 (t, J=1.6 Hz, 1H), 2.09 (s, 3H), 2.00 (s, 3H), 1.19-1.00 (m, 24H) ppm. $^{13}$C{$^1$H} NMR (100 MHz, CDCl$_3$, major) δ: 12.2, 14.4, 14.5, 14.6, 14.7, 18.2, 45.9, 46.0, 61.3, 124.6, 124.8, 124.9, 125.2, 125.4, 125.5, 127.1, 128.91, 128.92, 131.82, 131.84, 133.7, 133.8, 134.0, 134.3, 134.5, 134.60, 134.64, 135.2, 135.7, 135.9, 136.3, 136.5, 136.8, 136.9, 137.6, 137.9, 139.6, 140.0, 141.2, 141.6 ppm. HRMS (ESI, m/z): calcd for [C$_{31}$H$_{44}$NOS$_2$Si]$^+$ (M+NH$_4$)$^+$, 538.2628; found, 538.2621.

Endo-2-(2-hydroxyethyl)-4-(2-methyl-5-(((triisopropylsilyl)oxy)methyl)thiophen-3-yl)-5-(2-methyl-5-phenylthiophen-3-yl)-3a,4,7,7a-tetrahydro-1H-4,7-methanoisoindole-1,3(2H)-dione (6)

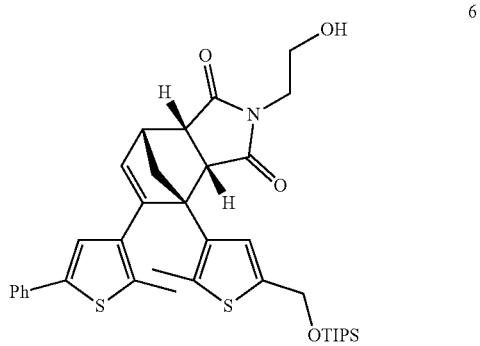

The cyclopentadiene mixture containing compound 5 (837 mg, 1.61 mmol) was combined with N-(2-hydroxyethyl)maleimide (see also Heo, Y. et al. Adv. Funct. Mater. 2014, 24, 5261-5268, the disclosure of which is incorporated herein by reference) (273 mg, 1.93 mmol) and DCM (3.0 mL) under nitrogen in a 20 mL vial and stirred at room temperature for 12 h. The crude product mixture was separated by column chromatography (30-100% EtOAc/Hexanes) and the fraction containing the title compound was further purified by SFC with 18% isopropanol/CO$_2$ as eluent to provide 6 as a white foaming solid (215 mg, 20%).

$R_f$=0.38 (EtOAc:hexanes 1:4). $^1$H NMR (500 MHz, CD$_2$Cl$_2$) δ: 7.48 (s, 1H), 7.30-7.23 (m, 4H), 7.22-7.14 (m, 1H), 6.54 (s, 1H), 6.18 (d, J=3.1 Hz, 1H), 4.99 (s, 2H), 3.97 (d, 1=7.7 Hz, 1H), 3.60 (m, 1H), 3.57-3.52 (m, 1H), 3.50-3.36 (m, 2H), 3.35-3.17 (m, 2H), 2.54 (dd, J=9.1, 1.8 Hz, 1H), 2.48 (s, 3H), 2.02 (s, 3H), 1.80 (dt, J=9.1, 1.2 Hz, 1H), 1.22-1.07 (m, 21H) ppm. $^{13}$C{$^1$H} NMR (100 MHz, CD$_2$Cl$_2$) δ: 12.6, 14.7, 15.9, 18.4, 41.7, 44.5, 48.9, 49.5, 58.1, 60.8, 61.8, 62.5, 124.6, 125.7, 126.8, 127.4, 129.3, 130.4, 132.6, 134.4, 134.8, 135.8, 136.8, 138.3, 141.2, 145.0, 177.9, 178.1 ppm. HRMS (ESI, m/z): calcd for [C$_{37}$H$_{51}$N$_2$O$_4$S$_2$Si]$^+$ (M+NH$_4$)$^+$, 679.3054; found, 679.3035.

Endo-2-(2-hydroxyethyl)-4-(5-(hydroxymethyl)-2-methylthiophen-3-yl)-5-(2-methyl-5-phenylthiophen-3-yl)-3a,4,7,7a-tetrahydro-1H-4,7-methanoisoindole-1,3(2H)-dione (7)

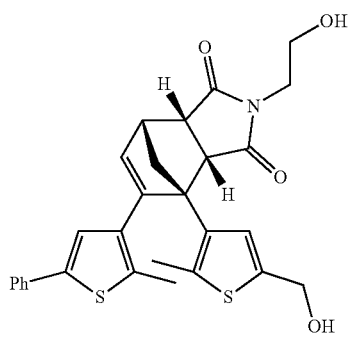

Diels-Alder adduct 6 (105 mg, 0.159 mmol) was dissolved in anhydrous THF (3 mL) in an oven-dried vial equipped with a stir bar and septum. The solution was cooled to 0° C. followed by the dropwise addition of tetra-n-butylammonium fluoride (1 M in THF, 0.23 mL, 0.23 mmol). After stirring at 0° C. for 2 h, the reaction mixture was poured into aqueous ammonium chloride (10%, 50 mL) and extracted with ethyl acetate (50 mL). The organic phase was washed with brine (50 mL), dried over Na$_2$SO$_4$, and concentrated under reduced pressure. The crude product was purified by column chromatography (0-10% MeOH/EtOAc) to afford the title compound as a white solid (78 mg, 97%). $R_f$=0.18 (EtOAc:hexanes 4:1). $^1$H NMR (400 MHz, CD$_2$Cl$_2$) δ: 7.57 (s, 1H), 7.30-7.23 (m, 4H), 7.22-7.14 (m, 1H), 6.50 (s, 1H), 6.18 (d, J=3.2 Hz, 1H), 4.86-4.74 (m, 2H), 3.96 (d, J=7.6 Hz, 1H), 3.60 (dd, J=7.6, 4.7 Hz, 1H), 3.57-3.53 (m, 1H), 3.48-3.34 (m, 2H), 3.34-3.17 (m, 2H), 2.55 (dd, J=9.1, 1.8 Hz, 1H), 2.48 (s, 3H), 2.06 (br s, 1H), 2.02 (s, 3H), 1.80 (dt, J=9.1, 1.2 Hz, 1H), 1.63 (br t, J=6.1 Hz, 1H) ppm. $^{13}$C{$^1$H} NMR (100 MHz, CD$_2$Cl$_2$) δ: 14.8, 15.9, 41.6, 44.5, 48.9, 49.5, 58.0, 60.4, 60.7, 62.4, 124.6, 125.7, 127.5, 129.2, 129.3, 130.4, 132.5, 134.8, 135.0, 136.9, 137.2, 138.3, 140.0, 144.9, 178.00, 178.05 ppm. HRMS (ESI, m/z): calcd for [C$_{28}$H$_{26}$NO$_3$S$_2$]$^+$ (M-OH)$^+$, 488.1349; found, 488.1363. The structure of 7 was confirmed by single crystal X-ray diffraction.

Endo-(4-(2-(2-((2-bromo-2-methyl propanoyl)oxy)ethyl)-5-(2-methyl-5-phenylthiophen-3-yl)-1,3-dioxo-1,2,3,3a,7,7a-hexahydro-4H-4,7-methanoisoindol-4-yl)-5-methylthiophen-2-yl)methyl 2-bromo-2-methylpropanoate (8)

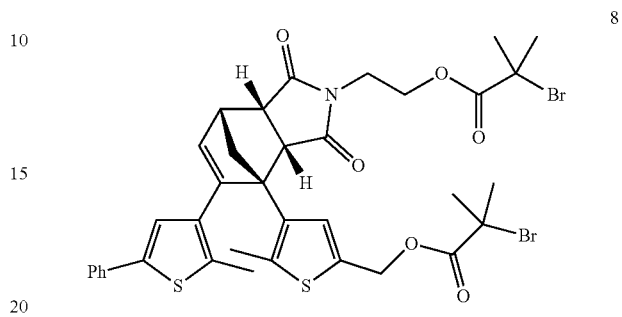

Diol 7 (49 mg, 0.097 mmol) was combined with triethylamine (70 μL, 0.50 mmol) and anhydrous THF (3 mL) in an oven-dried round bottom flask equipped with a stir bar and septum. The flask was cooled to 0° C. in an ice bath followed by the dropwise addition of α-bromoisobutyryl bromide (36 μL, 0.29 mmol). After stirring at 0° C. for 12 h, the reaction was poured into sat. aqueous NH$_4$Cl (20 mL) and extracted with ethyl acetate (20 mL). The organic layer was washed with brine, dried over Na$_2$SO$_4$, and concentrated under reduced pressure. The crude product was purified by column chromatography (0-30% EtOAc/hexanes) to provide the title compound as a white solid (68 mg, 88%). $R_f$=0.14 (EtOAc:hexanes 1:4). $^1$H NMR (400 MHz, CDCl$_3$) δ: 7.63 (s, 1H), 7.31-7.23 (m, 4H), 7.20-7.14 (m, 1H), 6.50 (s, 1H), 6.16 (d, J=3.0 Hz, 1H), 5.35 (ABq, Δv$_{AB}$=36 Hz, J$_{AB}$=12.7 Hz, 2H), 4.17-4.08 (m, 1H), 3.96 (d, J=7.5 Hz), 3.89-3.79 (m, 1H), 3.65-3.51 (m, 4H), 2.55 (dd, J=9.1, 1.6 Hz, 1H), 2.48 (s, 3H), 2.03 (s, 3H), 1.90 (s, 6H), 1.89 (s, 3H), 1.87 (s, 3H), 1.81 (d, J=9.1 Hz, 1H) ppm. $^{13}$C {$^1$H} NMR (100 MHz, CDCl$_3$) δ: 14.6, 15.5, 30.8, 30.9, 37.3, 44.0, 48.5, 49.2, 55.77, 55.83, 58.1, 61.9, 62.6, 62.7, 123.8, 125.4, 127.0, 128.9, 129.7, 131.1, 132.0, 132.6, 134.3, 134.4, 136.1, 138.3, 138.4, 144.9, 171.5, 171.6, 176.7, 176.8 ppm. HRMS (ESI, m/z): calcd for [C$_{36}$H$_{41}$Br$_2$N$_2$O$_6$S$_2$]$^+$ (M+NH$_4$)$^+$, 819.0767; found, 819.0754.

Poly(Methyl Acrylate) (PMA) Containing a Chain-Centered Cyclopentadiene-Maleimide Adduct (1)

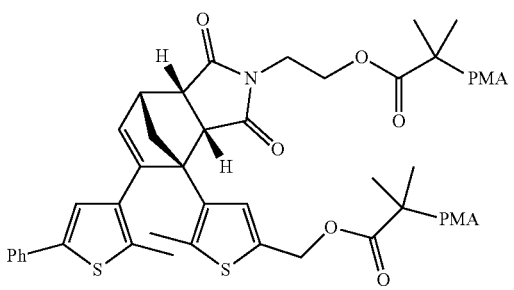

A 10 mL oven-dried Schlenk flask equipped with a stir bar and a PTFE valve was charged with initiator 8 (7.1 mg, 8.8 µmol), DMSO (1.2 mL), methyl acrylate (1.2 mL, 13.3 mmol), and Me$_6$TREN (3.5 mg, 15.2 µmol). The flask was sealed, the solution was deoxygenated via three freeze-pump-thaw cycles, and then backfilled with nitrogen. The flask was opened briefly and freshly cut copper wire (1.0 cm length, 20 gauge) was added to the frozen mixture under a blanket of nitrogen. The flask was resealed with a septum, evacuated for an additional 15 min, warmed to room temperature, and backfilled with nitrogen. After stirring at room temperature for 90 min, the flask was opened to air and the solution was diluted with DCM. The polymer solution was precipitated into cold methanol (3×) and the isolated material was dried thoroughly under vacuum to provide 0.55 g of polymer (48%). $M_n$=90 kg/mol; Đ=1.09.

Endo-2-(4-(2-methyl-5-(((triisopropylsilyl)oxy)methyl)thiophen-3-yl)-5-(2-methyl-5-phenylthiophen-3-yl)-1,3-dioxo-1,3,3a,4,7,7a-hexahydro-2H-4,7-methanoisoindol-2-yl)ethyl 2-bromo-2-methylpropanoate (9)

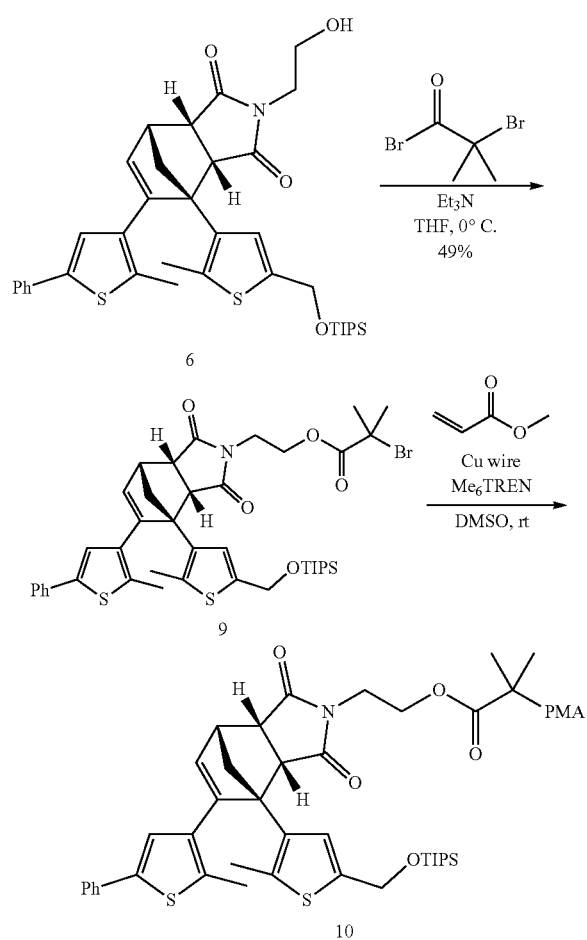

A flame-dried vial equipped with a stir bar and septum was charged with diarylethene 6 (70 mg, 0.11 mmol), triethylamine (20 µL, 0.30 mmol), and anhydrous THF (2 mL). The solution was cooled to 0° C. in an ice bath followed by the addition of α-bromoisobutyryl bromide (15.0 µL, 0.23 mmol). After stirring at 0° C. overnight, the crude material was purified by column chromatography to afford the title compound as a light brown solid (44 mg, 49%). R$_f$=0.33 (EtOAc:hexanes 1:4). $^1$H NMR (400 MHz, CD$_2$Cl$_2$) δ: 7.46 (s, 1H), 7.30-7.22 (m, 4H), 7.20-7.14 (m, 1H), 6.54 (s, 1H), 6.17 (d, J=3.1 Hz, 1H), 4.99 (s, 1H), 4.09-4.01 (m, 1H), 3.96 (d, J=7.7 Hz, 1H), 3.84-3.75 (m, 1H), 3.61-3.49 (m, 4H), 2.56 (dd, J=9.1, 1.8 Hz, 1H), 2.48 (s, 3H), 2.02 (s, 3H), 1.86 (s, 3H), 1.85 (s, 3H), 1.80 (d, J=9.0 Hz, 1H), 1.22-1.14 (m, 3H), 1.13-1.06 (m, 18H) ppm. $^{13}$C{$^1$H} NMR (100 MHz, CD$_2$Cl$_2$) δ: 12.6, 14.8, 15.8, 18.4, 31.0, 37.4, 44.5, 48.9, 49.7, 56.6, 58.4, 61.8, 62.4, 63.0, 124.7, 125.7, 126.9, 127.4, 129.3, 130.2, 132.8, 134.4, 135.0, 135.8, 136.7, 138.2, 141.1, 145.3, 171.7, 177.15, 177.24 ppm. HRMS (ESI, m/z): calcd for [C$_{41}$H$_{56}$BrN$_2$O$_5$S$_2$Si]$^+$ (M+NH$_4$)$^+$, 827.2578; found, 827.2547.

Control Polymer (PMA) Containing a Chain-End Functional Cyclopentadiene-Maleimide Adduct (10).

A 10 mL oven-dried Schlenk flask equipped with a stir bar and a PTFE valve was charged with initiator 9 (6.6 mg, 8.1 µmol), DMSO (1.1 mL), methyl acrylate (1.1 mL, 12.2 mmol), and Me$_6$TREN (3.5 mg, 15.2 µmol). The flask was sealed, the solution was deoxygenated via three freeze-pump-thaw cycles, and then backfilled with nitrogen. The flask was opened briefly and freshly cut copper wire (0.9 cm length, 20 gauge) was added to the frozen mixture under a blanket of nitrogen. The flask was resealed with a septum, evacuated for an additional 15 min, warmed to room temperature, and backfilled with nitrogen. After stirring at room temperature for 95 min, the flask was opened to air and the solution was diluted with DCM. The polymer solution was precipitated into cold methanol (3×) and the isolated material was dried thoroughly under vacuum to provide 0.52 g of polymer (49%). $M_n$=93 kg/mol; Đ=1.08.

Sonication Experiments and UV-Vis Spectroscopy

General procedure for ultrasonication experiments. An oven-dried sonication vessel was fitted with rubber septa, placed onto the sonication probe, and allowed to cool under a stream of dry argon. The vessel was charged with a solution of the polymer in anhydrous THF (2.0 mg/mL, 16-18 mL) and submerged in an ice bath maintained at 0° C. The solution was sparged continuously with argon beginning 20 min prior to sonication and for the duration of the sonication experiment. Pulsed ultrasound (1.0 sec on, 2.0 sec off, 25% amplitude, 11.0 W/cm$^2$) was then applied to the system. Aliquots (0.6-1.0 mL) were removed at 0, 10, 30, 50, 70, and 90 min (sonication "on" time) and filtered through a 0.45 µm syringe filter prior to analysis by GPC and UV-vis spectroscopy. Ultrasonic intensity was calibrated using the method described in Berkowski, K. L. et al. *Macromolecules* 2005, 38, 8975-8978, the disclosure of which is incorporated herein by reference.

GPC Analysis of Sonicated Samples.

A portion of the ultrasonicated sample was analyzed directly by GPC, monitored with a multi-angle light scattering (MALS) detector and a refractive index (RI) detector. To examine the photochromic behavior of the polymer after ultrasound-induced mechanical activation, a series of samples were exposed to UV light (λ=311 nm) for 1 min in a 2 mL glass autosampler vial prior to injection on the GPC. The samples were monitored with a UV-vis detector set at 505 nm with a detection bandwidth of 90 nm. All UV-irradiated samples were protected from exposure to visible light.

Analysis by UV-Vis Spectroscopy.

A portion of the ultrasonicated samples was added to a quartz microcuvette (5 mm path length) and the absorption spectrum was measured. The solution was then irradiated with UV light ($\lambda$=311 nm) in air and another absorption spectrum was immediately obtained. To determine an appropriate irradiation time, a range of exposure times was tested on a sample that was sonicated for 70 minutes (FIG. 5D). After 25 s of irradiation, the material approaches the photostationary state.

Analysis of Photochemical Reversibility.

To investigate the photoswitching properties of 1 after mechanochemical activation, a portion of the sonicated sample was added to a quartz cuvette (10 mm path length) equipped with a septum cap, which was then purged with nitrogen. The solution was irradiated in an alternating fashion with UV light for 25 s followed by white light for 2 min using the flashlight of a Galaxy S7 device. This sequence was repeated for multiple cycles and the absorption spectrum was measured immediately after each irradiation (FIG. 5G).

Determination of Sonication-Induced Chain Cleavage Rate

Sonication experiments were performed for 1 following the general procedure and the number average molecular weight ($M_n$) was measured at each time point by GPC using a multi-angle light scattering detector. Four replicate experiments were performed with each data point representing the average $M_n$ and the standard deviation of the measurements. The rate constant of polymer cleavage (k') was calculated from the slope of the least squares linear regression of the data according to the method described in Kryger, M. J. et al. *J. Am. Chem. Soc.* 2011, 133, 18992-18998, the disclosure of which is incorporated herein by reference, using eq 1:

$$\frac{1}{M_t} - \frac{1}{M_i} = k't \quad (1)$$

where $M_t$ is the number average molecular weight of the sonicated sample at time t, $M_i$ is the initial number average molecular weight of the polymer, and k' is the apparent rate constant of polymer cleavage. Note that k' accounts for the molecular weight of the monomer unit, $M_0$ (k'=k/$M_0$).

CoGEF Calculations

CoGEF calculations were performed using Spartan '16 Parallel Suite according to previously reported methods (see also: Beyer, M. K. *J. Chem. Phys.* 2000, 112, 7307-7312 and Robb, M. J. et al. *J. Am. Chem. Soc.* 2016, 138, 12328-12331, the disclosures of which are incorporated herein by reference). Ground state energies were calculated using DFT at the B3LYP/6-31G* level of theory. Starting from the equilibrium geometry of the unconstrained molecule (Energy=0 kJ/mol), the distance between the terminal methyl groups of the truncated structure was increased in increments of 0.05 Å and the energy was minimized at each step (FIG. 3A). The maximum force associated with the retro Diels-Alder reaction was calculated from the slope of the curve immediately prior to bond cleavage.

Single Crystal X-Ray Diffraction

Crystals for X-ray diffraction analysis were grown by slow diffusion of hexanes into a solution of compound 7 in toluene. A crystal was mounted on a polyimide MiTeGen loop with STP Oil Treatment and placed under a nitrogen stream. Low temperature (100 K) X-ray data were collected with a Bruker AXS D8 VENTURE KAPPA diffractometer running at 50 kV and 1 mA (Mo K$\alpha$=0.71073 Å; PHOTON II CPAD detector and Helios focusing multilayer mirror optics). All diffractometer manipulations, including data collection, integration, and scaling were carried out using the Bruker APEX3 software. An absorption correction was applied using SADABS. The space group was determined and the structure solved by intrinsic phasing using XT. Refinement was full-matrix least squares on F2 using XL. All non-hydrogen atoms were refined using anisotropic displacement parameters. Hydrogen atoms were placed in idealized positions and refined using a riding model. The isotropic displacement parameters of all hydrogen atoms were fixed at 1.2 times (1.5 times for methyl groups) the Ueq value of the bonded atom. Special refinement details: compound 7 crystallizes in the monoclinic space group P2$_1$/c (#14) with the asymmetric unit consisting of two molecules along with one toluene and 1.08 water molecules. Four non-hydrogen atoms of one molecule are disordered 92:8; a water is associated with the minor component.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A mechanically-gated photoswitch comprising
a mechanophore comprising a Diels-Alder adduct of a diarylethene and a dienophile, wherein the mechanophore is characterized by an ability to undergo a retro [4+2] cycloaddition reaction upon application of a mechanical force to re-produce the diarylethene and the dienophile; and wherein
the diarylethene comprises at least a cyclic diene moiety and two aryl moieties, each attached to each end of one of two carbon-carbon double bonds of the cyclic diene moiety; wherein
the mechanophore is embedded into a polymer, such that at least one chain of the polymer is covalently attached to a part of the Diels-Alder adduct corresponding to the diarylethene, and at least one additional chain of the polymer is covalently attached to a part of the Diels-Alder adduct corresponding to the dienophile; and wherein
the diarylethene is characterized by an ability to accomplish a switch between a ring opened and a ring closed state upon irradiation with light.

2. The mechanically-gated photoswitch of claim 1, wherein the switch between the ring opened and the ring closed state is accompanied by a change in spectral properties.

3. The mechanically-gated photoswitch of claim 2, wherein the cyclic diene moiety is a cyclopentadiene or a heterocyclic pentadiene.

4. The mechanically-gated photoswitch of claim 2, wherein the spectral properties is absorption of light comprising a visible wavelength.

5. The mechanically-gated photoswitch of claim 1, wherein the cyclic diene moiety comprises at least one X, wherein each of the at least one X is a substituted or unsubstituted chemical element independently selected from the group comprising of: $CR_2$, O, S, NR; and wherein R is a functionality further independently selected from the group comprising of: H, halogen, alkyl, alkoxy, alkylamine, aryl, heteroaryl, carbonyl, alkenyl, and any combination thereof.

6. The mechanically-gated photoswitch of claim 1, wherein the cyclic diene moiety is further substituted at any available position around its ring with at least one functionality $R_{cd}$, wherein each of the at least one $R_{cd}$ is independently selected from the group consisting of: H, halogen, alkyl, aryl, heteroaryl, alkoxy, alkylamine, alkenyl, carbonyl, a polymer chain of any composition, and any combination thereof.

7. The mechanically-gated photoswitch of claim 1, wherein the two aryl moieties are each independently selected from the group consisting of: a substituted or unsubstituted aryl; a substituted or unsubstituted heteroaryl.

8. The mechanically-gated photoswitch of claim 1, wherein the two aryl moieties are the same aromatic moiety.

9. The mechanically-gated photoswitch of claim 8, wherein the dienophile is a substituted alkene selected from the group consisting of: a maleimide, an acrylate, a methacrylate, a maleate, and a fumarate.

10. The mechanically-gated photoswitch of claim 1, wherein the dienophile is a substituted alkene, substituted with at least one functionality $R_{dp}$, wherein each of the at least one $R_{dp}$ is independently selected from the group consisting of: H, halogen, alkyl, aryl, heteroaryl, alkoxy, alkylamine, carbonyl, alkenyl, a polymer chain of any composition, and any combination thereof.

11. The mechanically-gated photoswitch of claim 1, wherein the at least one chain of the polymer and the at least one additional chain of the polymer embedding the mechanophore are of approximately the same length.

12. The mechanically-gated photoswitch of claim 1, wherein the polymer comprises a polymeric network of chains.

13. The mechanically-gated photoswitch of claim 1, wherein the polymer is selected from the group consisting of: polymethacrylate, polyacrylate, silicone, polyether, polyurethane, polycarbonate, polystyrene, and any combination thereof.

14. The mechanically-gated photoswitch of claim 1, wherein the switch between the ring opened and the ring closed state is reversible upon exposure to light and at least one other stimulus.

15. The mechanically-gated photoswitch of claim 14, wherein the at least one other stimulus is selected from the group consisting of: visible light, light of another wavelength, thermal energy, and any combination thereof.

16. The mechanically-gated photoswitch of claim 1, wherein the mechanically-gated photoswitch has the formula:

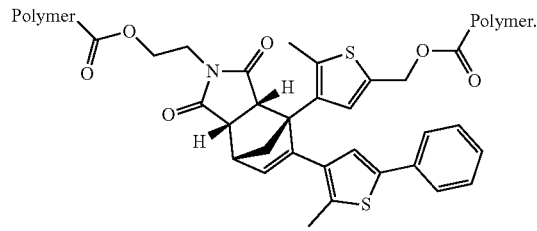

17. A method of mechanochemically-gating a photoswitchable molecular system comprising:
providing a mechanically-gated photoswitch comprising
a mechanophore comprising a Diels-Alder adduct of a diarylethene and a dienophile, wherein the mechanophore is characterized by an ability to undergo a retro [4+2] cycloaddition reaction upon application of a mechanical force to re-produce the diarylethene and the dienophile; and wherein
the diarylethene comprises at least a cyclic diene moiety and two aryl moieties, each attached to each end of one of two carbon-carbon double bonds of the cyclic diene moiety; wherein
the mechanophore is embedded into a polymer, such that at least one chain of the polymer is covalently attached to a part of the Diels-Alder adduct corresponding to the diarylethene, and at least one additional chain of the polymer is covalently attached to a part of the Diels-Alder adduct corresponding to the dienophile; and wherein
the diarylethene is characterized by an ability to accomplish a switch between a ring opened and a ring closed state upon irradiation with light; and
applying the mechanical force to the mechanically-gated photoswitch for a period of time, such that the polymer transduces the mechanical force to the mechanophore and activates the mechanophore to reveal the diarylethene.

18. The method of claim 17, wherein the switch between the ring opened and the ring closed state is accompanied by a change in spectral properties.

19. The method of claim 17, wherein the diarylethene is further irradiated with light to accomplish the switch.

20. The method of claim 17, wherein the switch between the ring opened and the ring closed state is reversible upon exposure to light and at least one other stimulus.

21. The method of claim 20, wherein the at least one other stimulus is selected from the group consisting of: visible light, light of another wavelength, thermal energy, and any combination thereof.

22. The method of claim 17, wherein applying the mechanical force comprises deforming the polymer.

23. The method of claim 22, wherein deforming the polymer is a method selected from the group consisting of: application of tension, compression, shearing, stretching, grinding, and any combination thereof.

24. The method of claim 17, wherein the cyclic diene moiety comprises at least one X, wherein each of the at least one X is a substituted or unsubstituted chemical element independently selected from the group comprising of: $CR_2$, O, S, NR; and wherein R is a functionality further independently selected from the group comprising of: H, halogen, alkyl, alkoxy, alkylamine, aryl, heteroaryl, alkenyl, carboxyl, and any combination thereof.

25. The method of claim 24, wherein the cyclic diene moiety is a cyclopentadiene or a heterocyclic pentadiene.

26. The method of claim 17, wherein the two aryl moieties are each independently selected from the group consisting of: an substituted or unsubstituted aryl; a substituted or unsubstituted heteroaryl.

27. A method for stress visualization in a material with mechanical stress visualization capabilities comprising:
providing a polymeric material with mechanical stress visualization capabilities comprising:
a polymer comprising a plurality of covalently embedded mechanically-gated photoswitches, wherein each mechanically-gated photoswitch comprises:

a mechanophore comprising a Diels-Alder adduct of a diarylethene and a dienophile, wherein the mechanophore is characterized by an ability to undergo a retro [4+2] cycloaddition reaction upon application of a mechanical force to re-produce the diarylethene and the dienophile; and wherein
  the diarylethene comprises at least a cyclic diene moiety and two aryl moieties, each attached to each end of one of two carbon-carbon double bonds of the cyclic diene moiety; wherein
the mechanophore is embedded into the polymer, such that at least one chain of the polymer is covalently attached to a part of the Diels-Alder adduct corresponding to the diarylethene, and at least one additional chain of the polymer is covalently attached to a part of the Diels-Alder adduct corresponding to the dienophile; and wherein
the diarylethene is characterized by an ability to accomplish a switch between a ring opened and a ring closed state upon irradiation with light, such that the switch is accompanied by a change in spectral properties;
applying the mechanical force to the polymeric material with mechanical stress visualization capabilities in a pattern for a period of time, such that the polymer transduces the mechanical force to the mechanophores of the plurality of covalently embedded mechanically-gated photoswitches, and activates the mechanophores to reveal the diarylethenes; and
irradiating the polymeric material with mechanical stress visualization capabilities with light to accomplish the switch and reveal the pattern.

28. The method of claim 27, wherein the switch accomplished by the diarylethene is reversible upon exposure to light and at least one other stimulus.

29. The method of claim 28, wherein the at least one other stimulus is selected from the group consisting of: visible light, light of another wavelength, thermal energy, and any combination thereof.

\* \* \* \* \*